(12) United States Patent
Tong et al.

(10) Patent No.: US 7,253,189 B2
(45) Date of Patent: Aug. 7, 2007

(54) CANNABINOID RECEPTOR LIGANDS

(75) Inventors: Ling Tong, Warren, NJ (US); Lei Chen, Roselle Park, NJ (US); Bandarpalle B. Shankar, Branchburg, NJ (US); Joseph A. Kozlowski, Princeton, NJ (US); Neng-Yang Shih, North Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 110 days.

(21) Appl. No.: 10/721,015

(22) Filed: Nov. 21, 2003

(65) Prior Publication Data

US 2004/0132804 A1 Jul. 8, 2004

Related U.S. Application Data

(60) Provisional application No. 60/428,861, filed on Nov. 25, 2002.

(51) Int. Cl.
*C07D 401/02* (2006.01)
*A61K 31/44* (2006.01)

(52) U.S. Cl. ............... 514/339; 514/347; 514/351; 514/415; 514/648; 546/277.4; 546/294; 548/400; 564/336

(58) Field of Classification Search ............ 514/351, 514/339, 347, 415, 648; 548/300, 452, 400; 564/336; 546/294, 277.4
See application file for complete search history.

(56) References Cited

U.S. PATENT DOCUMENTS

| | | | |
|---|---|---|---|
| 5,338,753 A | 8/1994 | Burstein et al. | |
| 5,462,960 A | 10/1995 | Barth et al. | |
| 5,532,237 A | 7/1996 | Gallant et al. | |
| 5,925,768 A | 7/1999 | Barth et al. | |
| 5,948,777 A | 9/1999 | Bender et al. | |
| 5,990,170 A | 11/1999 | Della Valle et al. | |
| 6,013,648 A | 1/2000 | Rinaldi et al. | |
| 6,017,919 A | 1/2000 | Inaba et al. | |
| 2003/0096844 A1 | 5/2003 | Kozlowski et al. | |
| 2003/0232859 A1 | 12/2003 | Kozlowski et al. | |
| 2004/0010013 A1 | 1/2004 | Friary et al. | |

FOREIGN PATENT DOCUMENTS

| | | |
|---|---|---|
| WO | WO 98/00412 | 1/1998 |
| WO | WO 02/062750 A1 | 8/2002 |

OTHER PUBLICATIONS

International Search Report (PCTUS 03/37366) dated Apr. 27, 2004—4 Pages.

*Primary Examiner*—Zinna N. Davis
(74) *Attorney, Agent, or Firm*—Thomas A. Blinka; William Y. Lee

(57) ABSTRACT

A compound of the formula

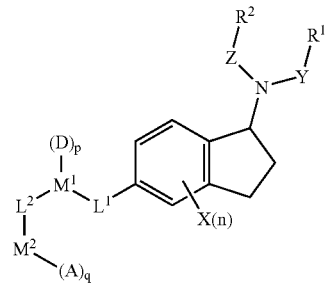

or a pharmaceutically acceptable salt or solvate thereof, wherein: $R^1$, $R^2$, $L^1$, $L^2$, $M^1$, $M^2$, n, p, q, A, D, X, Y and Z are as described in the specification; pharmaceutical compositions thereof, methods of making said pharmaceutical compositions; and methods of use thereof.

53 Claims, No Drawings

CANNABINOID RECEPTOR LIGANDS

CROSS-REFERENCE TO RELATED APPLICATION

This application claims the benefit of priority from U.S. Provisional Patent Application Ser. No. 60/428,861, filed Nov. 25, 2002.

BACKGROUND OF THE INVENTION

Field of the Invention

The present invention relates to compounds useful as cannabinoid receptor ligands that bind to cannabinoid ($CB_2$) receptors. Compounds according to the present invention can exhibit anti-inflammatory and immunomodulatory activity and can be useful in treating conditions characterized by inflammation and immunomodulatory irregularities. Examples of conditions that can be treated include, but are not limited to, rheumatoid arthritis, neuropathic pain, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation.

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

In one embodiment, the present invention provides a compound represented by the structural Formula (I):

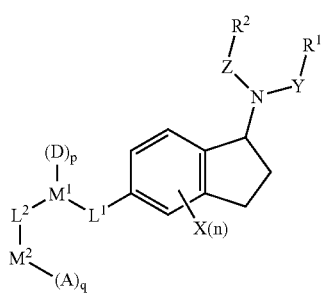

(I)

or a pharmaceutically acceptable salt or solvate thereof, wherein:

$R^1$ is selected from the group consisting of hydrogen, substituted or unsubstituted alkyl, —$CF_3$, substituted or unsubstituted alkoxy, —$N(R^3)_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with $(X)_t$ substituent(s);

$R^2$ is selected from the group consisting of hydrogen, substituted or unsubstituted alkyl, —$CF_3$, substituted or unsubstituted alkoxy, —$N(R^3)_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with $(X)_t$ substituent(s); or $R^1$ and $R^2$, taken together with Z, N and Y form a 4-8 membered substituted or unsubstituted heterocycloalkyl moiety, wherein the term "substituted" means being substituted with $(X)_t$ substituent(s);

each $R^3$, which can be the same or different, is independently selected from the group consisting of hydrogen, substituted or unsubstituted alkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein the term "substituted" means being substituted with $(X)_t$ substituent(s);

each X, when present, is independently selected from the group consisting of alkyl, alkenyl, alkynyl, cycloalkyl, heterocycloalkyl, aryl, heteroaryl, aminoalkyl-, —$NR^4R^5$, halo, —$CF_3$, —$OCF_2H$, —$OCF_3$, —$OR^6$, —$C(O)R^6$, —$C(O)OR^6$, —$NR^6C(O)R^7$, —$NR^6C(O)OR^7$, —$C(O)NR^4R^5$, —$NO_2$, —CN, —$S(O)_2R^6$, —$S(O)_2NR^4R^5$ and —$NR^4S(O)_2R^5$;

$R^4$ and $R^5$, which can be the same or different, are each independently selected from the group consisting of H or alkyl, or $R^4$ and $R^5$, taken together with N to which they are each attached, form a 4- to 8- membered heterocycloalkyl moiety optionally having an additional heteroatom selected from the group consisting of N, O and S, wherein the additional N heteroatom, when present, or any ring carbon atom of the heterocycloalkyl moiety can be substituted with H or alkyl;

$R^6$ and $R^7$, which can be the same or different, are each independently selected from the group consisting of H or alkyl;

$L^1$ is selected from the group consisting of —$C(R^2)_2$—, —OC(O)—, —C(O)—, —C(O)O—, —(CH($OR^2$))—, —$S(O)_2$—, —S(O)—, —S—, —O—, —$N(R^2)$—, —C(O)NH—, —NHC(O)—, —$CF_2$— and —C(=N—$OR^2$)—;

$L^2$ is selected from the group consisting of a covalent bond, —$C(R^2)_2$—, —C(=N—$OR^2$)—, —$S(O)_2$—, —S(O)—, —S—, —C(O)—, —O—, —$N(R^2)$, —C(O)NH—, —NHC(O)—, —OC(O)—, —C(O)O—, —(CH($OR^2$))— and —$CF_2$—;

$M^1$ is an aryl, heteroaryl, cycloalkyl or heterocycloalkyl moiety wherein said aryl, heteroaryl, cycloalkyl or heterocycloalkyl moiety is substituted with D when p is ≧1;

$M^2$ is an alkyl, cycloalkyl, heterocycloalkyl, aryl or heteroaryl moiety wherein said alkyl, cycloalkyl, heterocycloalkyl, aryl or heteroaryl moiety is substituted with A when q is ≧1;

m is 1-3;

n is 0-3 wherein when n>1, each X can be the same or different and is independently selected;

p is 0-4;

q is 0-5;

t is 0-6 wherein when t>1, each X can be the same or different and is independently selected;

v is 1-3;

A is an optional substituent on $M^2$, each A being independently selected from the group consisting of —Br, —Cl, —F, —CF$_3$, —OH, —OCF$_2$H, —OCF$_3$, alkoxy, substituted or unsubstituted alkyl, substituted or unsubstituted cycloalkyl, —O-substituted or unsubstituted cycloalkyl, substituted or unsubstituted heterocycloalkyl, substituted or unsubstituted aryl, substituted or unsubstituted heteroaryl, —CN, —NO$_2$, —C(O)OR$^4$, —C(O)NR$^4$R$^5$, —NR$^4$C(O)R$^5$, —NR$^4$R$^5$, and —S(O)$_2$R$^2$, wherein the term "substituted" means being substituted with $(X)_t$ and wherein when q>1, each A can be the same or different;

D is an optional substituent on $M^1$, each D being independently selected from the group consisting of —Br, —Cl, —F, —CF$_3$, —OH, —OCF$_2$H, —OCF$_3$, alkoxy, substituted or unsubstituted alkyl, substituted or unsubstituted cycloalkyl, —O-substituted or unsubstituted cycloalkyl, substituted or unsubstituted heterocycloalkyl, substituted or unsubstituted aryl, substituted or unsubstituted heteroaryl, —CN, —NO$_2$, —C(O)OR$^4$, —C(O)NR$^4$R$^5$, —NR$^4$C(O)R$^5$, —NR$^4$R$^5$, and —S(O)$_2$R$^2$, wherein the term "substituted" means being substituted with $(X)_n$ and wherein when p>1, each D can be the same or different;

Y is selected from the group consisting of a covalent bond, —(CR$^6$R$^7$)$_m$—, —S(O)$_2$—, and —C(O)—; and Z is selected from the group consisting of a covalent bond, —(CR$^6$R$^7$)$_v$—, —S(O)$_{0-2}$—, and —C(O)—, with the following provisos:

when $L^2$ is a covalent bond, $M^2$ is directly linked to $M^1$;

when Y is a covalent bond, $R^1$ is directly linked to the nitrogen atom of —N-Z-R$^2$; and when Z is a covalent bond, $R^2$ is directly linked to the nitrogen atom of —N—Y—R$^1$.

Another aspect of the invention relates to a pharmaceutical composition comprising one or more compounds of Formula (I), preferably with one or more pharmaceutically acceptable carriers.

Another aspect of the invention relates to a method of preparing a pharmaceutical composition comprising contacting one or more compounds of Formula (I) with one or more pharmaceutically acceptable carriers.

Another aspect of the invention relates to a method of modulating (inhibiting or activating) a cannabinoid CB$_2$ receptor in a patient in need of such modulation comprising administering to a patient having a CB$_2$ receptor a CB$_2$ receptor-modulating amount of one or more compounds of Formula (I).

Another aspect of the invention relates to a method of treating cancer, inflammatory diseases, immunomodulatory diseases, or respiratory diseases comprising administering to a patient in need of such treatment one or more compounds of Formula (I).

Another aspect of the invention relates to a method of treating cancer, inflammatory diseases, immunomodulatory diseases or respiratory diseases by co-administering or combining a compound of Formula (I) with one or more second agents which can be the same or different from each other, and are independently selected from the group consisting of DMARDS, NSAIDS, COX-2 inhibitors, COX-1 inhibitors, immunosuppressives, BRMs; and other anti-inflammatory agents.

Another aspect of the invention relates to a method of treating multiple sclerosis comprising co-administering or combining (1) at least one compound of Formula (I); and (2) one or more additional agents different from the compound of formula I which are independently selected from the group consisting of Interferon B1a, Interferon B1b and glatiramer acetate.

Another aspect of the invention relates to a kit for treating a disease selected from the group consisting of cancer, inflammatory diseases, immunomodulatory diseases, and respiratory diseases, comprising in one or more containers an active ingredient for modulating a cannabinoid CB$_2$ receptor in a patient in need of such modulation wherein said active ingredient comprises one or more compounds of Formula (I) and one or more pharmaceutically acceptable carriers.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

In its many embodiments, the present invention provides a class of compounds of general Formula (I) above, processes for producing such compounds, pharmaceutical formulations or compositions comprising one or more of such compounds, methods of preparing the same, and methods of treatment, prevention, inhibition or amelioration of one or more conditions or diseases associated with inflammation or immunomodulation or other conditions or diseases such as are discussed in detail below that can be useful as cannabinoid receptor ligands.

Referring to general Formula (I) above, $R^1$ is preferably selected from the group consisting of hydrogen, substituted or unsubstituted alkyl, —N(R$^3$)$_2$, substituted or unsubstituted cycloalkyl, substituted or unsubstituted aryl, substituted or unsubstituted heteroaryl and substituted or unsubstituted heterocycloalkyl, wherein the term "substituted" means being substituted with $(X)_t$ substituents, and t is 0-2.

More preferably, $R^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with $(X)_t$ substituents, and t is 0-2.

$R^2$ is preferably selected from the group consisting of hydrogen, substituted or unsubstituted alkyl, —N(R$^3$)$_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with $(X)_t$ substituents, and t is 0-2.

More preferably, $R^2$ is selected from the group consisting of hydrogen, substituted or unsubstituted alkyl, substituted or unsubstituted cycloalkyl, and substituted or unsubstituted heterocycloalkyl, wherein the term "substituted" means being substituted with $(X)_t$ substituents, and t is 0-2.

$R^3$ is preferably selected from the group consisting of hydrogen and substituted or unsubstituted alkyl, wherein the term "substituted" means being substituted with $(X)_t$ substituents, and t is 0-2. More preferably, $R^3$ is hydrogen.

X is preferably selected from the group consisting of alkyl, halo, —CF$_3$, —OCF$_3$, —OH and alkoxy, wherein each X can be the same or different and is independently selected when there is more than one X present.

$L^1$ is preferably selected from the group consisting of —C(R$^2$)$_2$—, —C(O)—, —S(O)$_2$—, —O—, —NR$^2$—, —C(O)NH—, —NHC(O), —CF$_2$— and —C(=N—OR$^2$)—. More preferably, $L^1$ is selected from the group consisting of —C(R$^2$)$_2$—, —C(O)—, and —S(O)$_2$—.

$L^2$ is preferably selected from the group consisting of a covalent bond, —C(R$^2$)$_2$—, —C(=N—OR$^2$)—, —S(O)$_2$—, —C(O)—, —O—, —N(R$^2$)—, —C(O)NH— and —NHC(O)—. More preferably, $L^2$ is selected from the group consisting of a covalent bond, —C(R$^2$)$_2$—, —S(O)$_2$—, and —C(O)—.

$M^1$ is preferably selected from the group consisting of aryl or heteroaryl, wherein said aryl or heteroaryl can be optionally substituted with D. Non-limiting examples of $M^1$ include a moiety selected from the group consisting of phenyl, indolyl, benzofuranyl, dihydrobenzofuranyl, furanyl, thienyl and pyridinyl.

$M^2$ is preferably an aryl or heteroaryl moiety wherein said aryl or heteroaryl moiety can be optionally substituted with A. Non-limiting examples of $M^2$ include a moiety selected from the group consisting of phenyl, furanyl, thienyl, quinolinyl and pyridinyl.

n is preferably 0-2.
p is preferably 0-2.
q is preferably 0-2.
t is preferably 0-2.

A, which can be the same or different when q>1, is preferably independently selected from the group consisting of —NR$^4$R$^5$, —Cl, —F, —CF$_3$, —OCF$_3$, alkoxy, substituted or unsubstituted alkyl, heteroaryl, and —S(O)$_2$R$^2$, wherein the term "substituted" means being substituted with (X)$_t$, and t is 0-2. More preferably, A, which can be the same or different when q>1, is independently selected from the group consisting of —NR$^4$R$^5$, —Cl, —F, —CF$_3$, —OCF$_3$, and substituted or unsubstituted alkyl, wherein the term "substituted" means being substituted with (X)$_t$, and t is 0-2.

D, which can be the same or different when p>1, is preferably independently selected from the group consisting of —Br, —Cl, —F, —CF$_3$, —OH, —OCF$_2$H, —OCF$_3$, alkoxy, substituted or unsubstituted alkyl, cycloalkyl, —O-cycloalkyl, substituted or unsubstituted heteroalkyl, heteroaryl, and —S(O)$_2$R$^2$, wherein the term "substituted" means being substituted with (X)$_n$, and n is 0-2. More preferably, D, which can be the same or different when p>1, is independently selected from the group consisting of —Cl, —F, —CF$_3$, —OCF$_2$H, —OCF$_3$, substituted or unsubstituted alkyl, cycloalkyl, and heteroaryl, wherein the term "substituted" means being substituted with (X)$_n$, and n is 0-2.

Y preferably represents —S(O)$_2$— or —C(O)—.

Exemplary compounds of formula 1 are set forth in Table I below wherein Z is a covalent bond, R$^2$ is H, n is 0, and R$^1$, L$^1$, L$^2$, M$^1$, M$^2$, q, p, A, D and Y are as defined in the following Table I:

TABLE I

| # | R$^1$ | q, A | M$^1$ (with linking points to L$^1$, L$^2$ and D) | M$^2$ (with linking points to L$^2$ and A) | L$^1$ | L$^2$ | Y | p, D |
|---|---|---|---|---|---|---|---|---|
| 1 | —CF$_3$ | 1, —F | phenyl (D, L$_1$, L$_2$) | phenyl (L$_2$, A) | —C(O)— | —S(O)$_2$— | —S(O)$_2$— | 1, —OCF$_3$ |
| 2 | —CH$_3$ | 1, —F | phenyl (D, L$_1$, L$_2$) | phenyl (L$_2$, A) | —C(O)— | —S(O)$_2$— | —S(O)$_2$— | 1, —OCF$_3$ |
| 3 | —CF$_3$ | 1, —F | phenyl (D, L$_1$, L$_2$) | phenyl (L$_2$, A) | —CH$_2$— | —S(O)$_2$— | —S(O)$_2$— | 1, —OCF$_3$ |
| 4 | —CF$_3$ | 1, —F | phenyl (D, L$_1$, L$_2$) | phenyl (L$_2$, A) | —CH$_2$— | —S(O)$_2$— | —S(O)$_2$— | 1, —OCF$_3$ |
| 5 | —CF$_3$ | 1, —F | phenyl (D, L$_1$, L$_2$) | phenyl (L$_2$, A) | —S(O)$_2$— | —S(O)$_2$— | —S(O)$_2$— | 1, —OCH$_3$ |

TABLE I-continued
| # | R¹ | q, A | M¹ (with linking points to L¹, L² and D) | M² (with linking points to L² and A) | L¹ | L² | Y | p, D |
|---|---|---|---|---|---|---|---|---|
| 6 | —CF₃ | 1, —F | 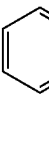 | 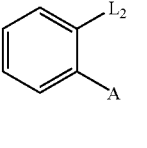 | —S(O)₂— | —S(O)₂— | —S(O)₂— | 1, —Cl |
| 7 | —CF₃ | 0 | 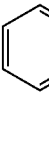 | 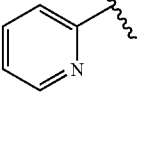 | —S(O)₂— | —S(O)₂— | —S(O)₂— | 1, —Cl |
| 8 | —CH₃ | 0 | 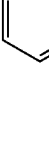 | 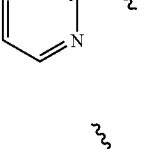 | —S(O)₂— | —S(O)₂— | —S(O)₂— | 1, —Cl |
| 9 | —CH₃ | 0 |  | 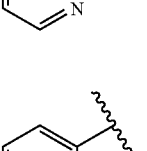 | —S(O)₂— | —S(O)₂— | —S(O)₂— | 1,  |
| 10 | —CH₃ | 0 | 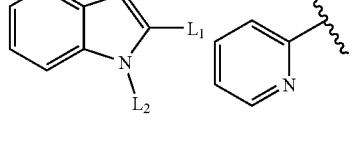 | 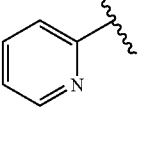 | —S(O)₂— | —S(O)₂— | —S(O)₂— | 0 |
| 11 | 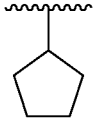 | 0 | 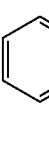 | 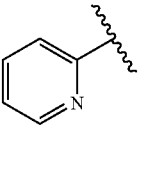 | —S(O)₂— | —S(O)₂— | Covalent bond | 1,  |
| 12 | —CF₃ | 0 | 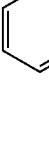 | 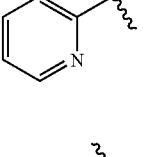 | —S(O)₂— | —S(O)₂— | —S(O)₂— | 1,  |
| 13 | 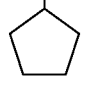 | 0 | 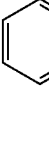 | 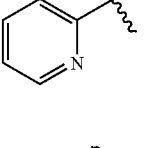 | —S(O)₂— | —S(O)₂— | —C(O)— | 1,  |
| 14 | 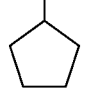 | 0 | 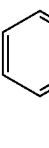 | 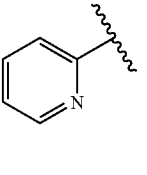 | —S(O)₂— | —S(O)₂— | Covalent bond | 1, Cl |

TABLE I-continued
| # | R¹ | q, A | M¹ (with linking points to L¹, L² and D) | M² (with linking points to L² and A) | L¹ | L² | Y | p, D |
|---|---|---|---|---|---|---|---|---|
| 15 | 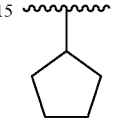 | 0 | 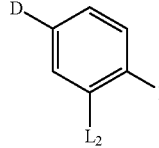 | 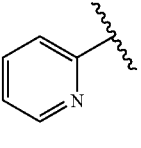 | —S(O)₂— | —S(O)₂— | —C(O)— | 1, Cl |
| 16 | 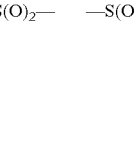 | 0 | 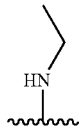 | 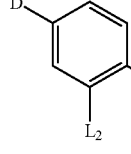 | —S(O)₂— | —S(O)₂— | —C(O)— | 1, Cl |
| 17 | —CF₃ | 0 | 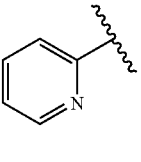 |  | —S(O)₂— | —S(O)₂— | —S(O)₂— | 0 |
| 18 | —CF₃ | 0 | 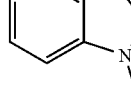 | 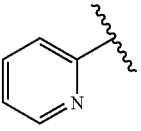 | —S(O)₂— | —S(O)₂— | —C(O)— |  |
| 19 | —CF₃ | 0 | 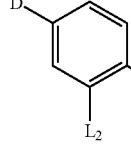 | 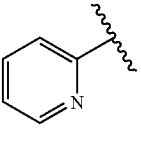 | —S(O)₂— | —S(O)₂— | —C(O)— | 1,  |
| 20 | —CF₃ | 0 |  | 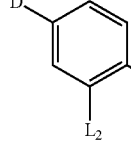 | —S(O)₂— | —S— | —C(O)— | 1, 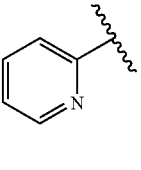 |
| 21 | —CF₃ | 1, F |  |  | —CH(OH)— | —S— | —C(O)— | 1, —OCF₃ |
| 22 | —CF₃ | 1, F | 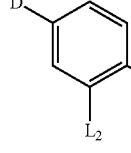 | 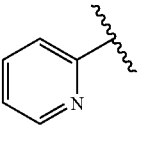 | —CH₂— | —S— | —C(O)— | 1, —OCF₃ |
| 23 | —CF₃ | 1, F |  |  | —CH₂— | —S(O)₂— | —C(O)— | 1, —OCF₃ |

In another embodiment, the present invention provides a compound represented by the structural Formula (IA):

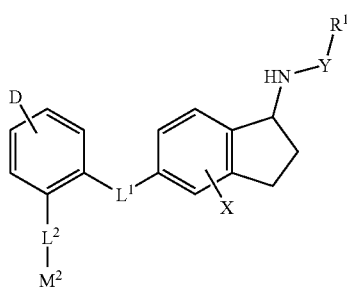

IA or a pharmaceutically acceptable salt or solvate thereof, wherein:
$R^1$ is selected from the group consisting of —$CF_3$, —$CH_3$, cyclopentyl, and —$NC_2H_5$;
X is selected from the group consisting of halo, —$CF_3$, —OH and —$OCF_3$;
Y is selected from the group consisting of —$S(O)_2$, —C(O)—, and a covalent bond;
$L_1$ is selected from the group consisting of —$S(O)_2$—, —$CH_2$— and —C(O)—;
$L_2$ is selected from the group consisting of —$S(O)_2$—, and —$CH_2$—;
D is selected from the group consisting of —$OCF_3$, —Cl, cyclopropyl, and isopropyl; and
$M^2$ is selected from the group consisting of pyridyl and 2-fluorophenyl.

In another embodiment, the present invention relates to compounds of Formula (IA), or pharmaceutically acceptable salts or solvates thereof, wherein $R^1$ is selected from the group consisting of —$CF_3$ and —$CH_3$;
X is selected from the group consisting of halo, —OH, —$CF_3$, and —$OCF_3$;
Y is —$S(O_2)$—;
$L_1$ is selected from the group consisting of —$S(O)_2$— and —$CH_2$—;
$L_2$ is —$S(O)_2$—;
D is selected from the group consisting of —$OCF_3$, —Cl, and cyclopropyl; and
$M^2$ is selected from the group consisting of pyridyl and 2-fluorophenyl.

In another embodiment, the present invention relates to compounds of Formula (IA), or pharmaceutically acceptable salts or solvates thereof, wherein $R^1$ is —$CF_3$; X is selected from the group consisting of halogen, —$CF_3$, —OH, and —$OCF_3$; Y is —$S(O)_2$—; $L_1$ is O, —$S(O)_2$—; $L_2$ is —$S(O)_2$—; D is selected the group consisting of —$OCF_3$, —Cl, and cyclopropyl; and $M^2$ is selected from the group consisting of pyridyl and 2-fluorophenyl.

In another embodiment, the present invention relates to a compound of formula (IB):

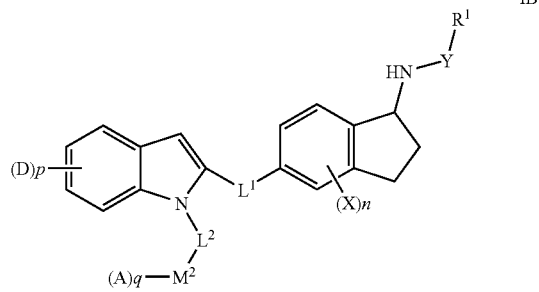

IB or a pharmaceutically acceptable salts or solvates thereof, wherein $R^1$ is selected from the group consisting of hydrogen, substituted or unsubstituted alkyl, —$N(R^3)_2$, substituted or unsubstituted cycloalkyl, substituted or unsubstituted aryl, substituted or unsubstituted heteroaryl and substituted or unsubstituted heterocycloalkyl, wherein the term "substituted" means being substituted with $(X)_t$, and t is 0-2; $R^3$ is selected from the group consisting of hydrogen and substituted or unsubstituted alkyl, wherein the term "substituted" means being substituted with $(X)_t$, and t is 0-2; X is selected from the group consisting of alkyl, halogen, —$CF_3$, —OH, —$OCF_3$, and alkoxy, wherein each X can be the same or different and is independently selected when there is more than one X present; Y represents —$S(O)_2$— or —C(O)—; $L^1$ is selected from the group consisting of —$C(R^2)_2$—, —C(O)—, —$S(O)_2$—, —O—, —$NR^2$—, —C(O)NH—, —NHC(O)—, —$CF_2$— and —C(=N—$OR^2$)—; $L^2$ is selected from the group consisting of a covalent bond, —$C(R^2)_2$—, —C(=N—$OR^2$)—, —$S(O)_2$—, —C(O)—, —O—, —$N(R^2)$—, —C(O)NH— and —NHC(O)—; $M^2$ is an aryl or heteroaryl moiety wherein said aryl or heteroaryl moiety can be optionally substituted with A; n is 0-2; p is 0-2; and q is 0-2.

In another embodiment, the present invention provides a compound represented by the structural Formula (IB), or a pharmaceutically acceptable salt or solvate thereof, wherein $R^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with $(X)_t$, and t is 0-2; $R^3$ is hydrogen; $L^1$ is selected from the group consisting of —$C(R^2)_2$—, —C(O)—, and —$S(O)_2$—; $L^2$ is selected from the group consisting of a covalent bond, —$C(R^2)_2$—, —$S(O)_2$—, and —C(O)—; X is selected from the group consisting of halogen, —$CF_3$, —OH, and —$OCF_3$, wherein each X can be the same or different and is independently selected when there are more than one X present; Y represents —$S(O)_2$— or —C(O)—; $M^2$, which can be optionally substituted with A, is a moiety selected from the group consisting of phenyl, furanyl, thienyl, quinolinyl and pyridinyl; n is 0-2; p is 0-2; and q is 0-2.

In another embodiment, the present invention relates to a compound of Formula (IB), wherein $R^1$ is —$CF_3$; X is selected from the group consisting of halo, —OH, —$CF_3$, and —$OCF_3$, wherein each X can be the same or different and is independently selected when there is more than one X present; Y is —$S(O)_2$—; $L_1$ is —$S(O)_2$—; $L_2$ is —$S(O)_2$—; and $M^2$ is selected from the group consisting of pyridyl and 2-fluorophenyl.

In another embodiment, the present invention provides a compound represented by the structural Formula (IC):

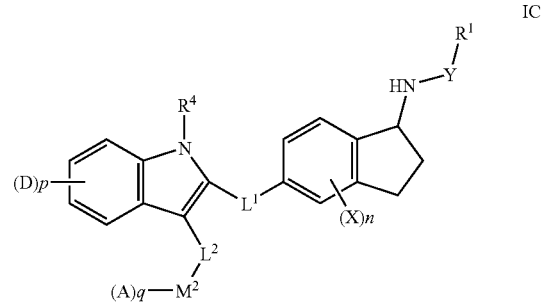

IC or a pharmaceutically acceptable salt or solvate thereof, wherein: $R^1$ is selected from the group consisting of hydrogen, substituted or unsubstituted alkyl, —$N(R^3)_2$, substituted or unsubstituted cycloalkyl, substituted or unsubstituted aryl, substituted or unsubstituted heteroaryl and substituted or unsubstituted heterocycloalkyl, wherein the term "substituted" means being substituted with $(X)_t$, and t is 0-2; $R^3$ is selected from the group consisting of hydrogen and substituted or unsubstituted alkyl, wherein the term "substituted" means being substituted with $(X)_t$, and t is 0-2; $R^4$ is hydrogen or alkyl; X is selected from the group consisting of alkyl, halogen, —$CF_3$, —OH, —$OCF_3$, and alkoxy, wherein each X can be the same or different and is independently selected when there is more than one X present; Y represents —$S(O)_2$— or —C(O)—; $L^1$ is selected from the group consisting of —$C(R^2)_2$—, —C(O)—, —$S(O)_2$—, —O—, —$NR^2$—, —C(O)NH—, —NHC(O)—, —$CF_2$— and —C(=N—$OR^2$)—; $L^2$ is selected from the group consisting of a covalent bond, —$C(R^2)_2$—, —C(=N—$OR^2$)—, —$S(O)_2$—, —C(O)—, —O—, —$N(R^2)$—, —C(O)NH— and —NHC(O)—; $M^2$ is an aryl or heteroaryl moiety wherein said aryl or heteroaryl moiety can be optionally substituted with A; n is 0-2; p is 0-2; and q is 0-2.

In another embodiment, the present invention relates to compounds of Formula (IC), or pharmaceutically acceptable salts or solvates thereof, wherein $R^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with $(X)_t$, and t is 0-2; $R^3$ is hydrogen; $R^4$ is hydrogen or alkyl; $L^1$ is selected from the group consisting of —$C(R^2)_2$—, —C(O)—, and —$S(O)_2$—; $L^2$ is selected from the group consisting of a covalent bond, —$C(R^2)_2$—, —$S(O)_2$—, and —C(O)—; X is selected from the group consisting of halogen, —$CF_3$, —OH, and —$OCF_3$, wherein each X can be the same or different and is independently selected when there are more than one X present; Y represents —$S(O)_2$— or —C(O)—; $M^2$, which can be optionally substituted with A, is a moiety selected from the group consisting of phenyl, furanyl, thienyl, quinolinyl and pyridinyl; n is 0-2; p is 0-2; and q is 0-2.

In another embodiment, the present invention relates to a compound of Formula (IC) wherein, $R^1$ is —$CF_3$; X is selected from the group consisting of halogen, —$CF_3$, —OH, and —$OCF_3$, wherein each X can be the same or different and is independently selected when there are more than one X present; Y is —$S(O)_2$—; $L_1$ is $S(O)_2$—; $L_2$ is —$S(O)_2$—; and $M^2$ is selected from the group consisting of pyridyl and 2-fluorophenyl.

In a preferred embodiment, the compound of the present invention is selected from the group consisting of:

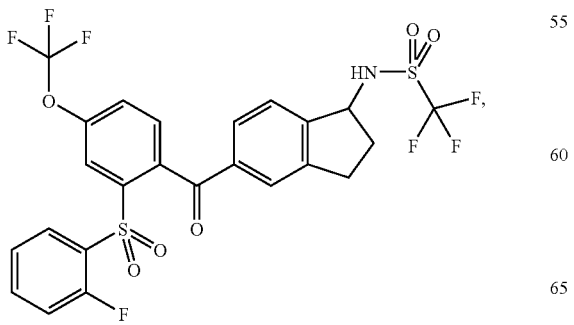

-continued

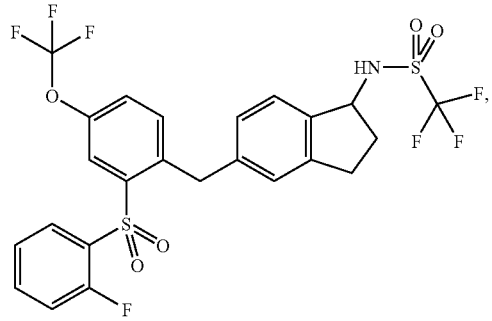

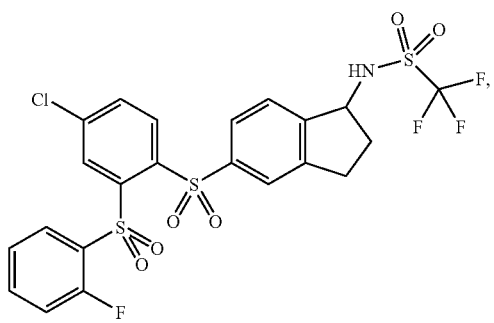

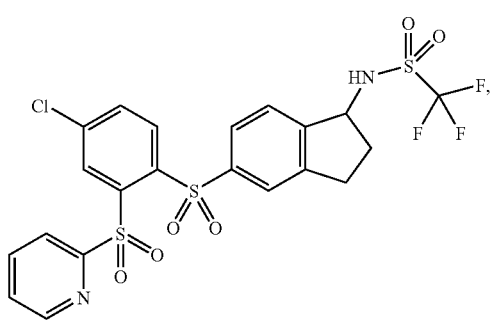

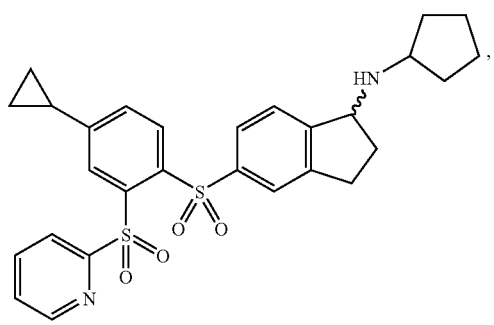

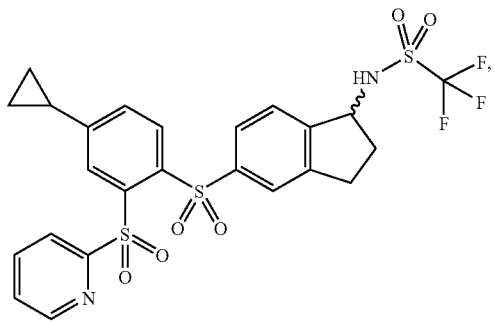

-continued

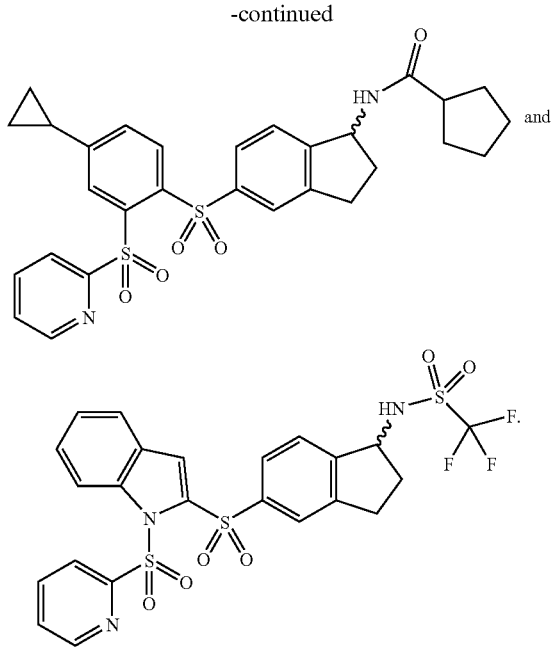

Cannabinoid receptor ligands according to the present invention can have anti-inflammatory activity and/or immunomodulatory activity and are useful in the treatment of various medical conditions including, e.g., treatment of neuropathic pain, rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma and bronchitis.

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

"Alkyl" means an aliphatic hydrocarbon group that may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having about 1 to about 6 carbon atoms in the chain that may be straight or branched. Preferred alkyl groups in the present invention are lower alkyl groups. Non-limiting examples of suitable alkyl groups include methyl, ethyl, n-propyl, isopropyl, n-butyl, t-butyl, n-pentyl, heptyl, nonyl, decyl, trifluoromethyl and cyclopropylmethyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 2 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain which may be straight or branched.

Non-limiting examples of suitable alkenyl groups include ethenyl, propenyl, n-butenyl, 3-methylbut-2-enyl, and n-pentenyl.

"Halo" means fluoro, chloro, bromo, or iodo groups. Preferred halo groups are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" or "halogenated alkyl" means alkyl having one or more halo atom substituents. Non-limiting examples include —$CH_2Cl$, —$CHCl_2$, —$CCl_3$, —$CH_2F$, —$CHF_2$, —$CF_3$, —$CH_2$—$CH_2Cl$, —$CH_2$—$CHCl_2$, and —$CHCl$—$CH_2Cl$.

"Heteroalkyl" means straight or branched alkyl chain as defined above comprising 1 or more heteroatoms, which can be the same or different, and are independently selected from the group consisting of N, O and S.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, phenylethyl and naphthalenylmethyl. The aralkyl is linked to an adjacent moiety through the alkyl.

"Alkylaryl" means an alkyl-aryl- group in which the alkyl and aryl are as previously described. Preferred alkylaryls comprise a lower alkyl group. Non-limiting examples of suitable alkylaryl groups include tolyl and xylyl. The alkylaryl is linked to an adjacent moiety through the aryl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The aryl group is linked to an adjacent moiety through the ether oxygen.

"Aralkyloxy" means an aralkyl-O— group in which the aralkyl group is as previously described. Non-limiting examples of suitable aralkyloxy groups include benzyloxy and naphthalenylmethoxy. The aralkyl group is linked to an adjacent moiety through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio and isopropylthio. The alkyl is linked to an adjacent moiety through the sulfur.

"Arylthio" means an aryl-S— group in which the aryl group is as previously described. Non-limiting examples of suitable arylthio groups include phenylthio and naphthylthio. The aryl is linked to an adjacent moiety through the sulfur.

"Aralkylthio" means an aralkyl-S— group in which the aralkyl group is as previously described. Non-limiting example of a suitable aralkylthio group is benzylthio. The aralkyl is linked to an adjacent moiety through the sulfur.

"Alkoxycarbonyl" means an alkyl-O—C(O)— group. Non-limiting examples of suitable alkoxycarbonyl groups include methoxycarbonyl and ethoxycarbonyl. The alkoxy is linked to an adjacent moiety through the carbonyl.

"Aryloxycarbonyl" means an aryl-O—C(O)— group. Non-limiting examples of suitable aryloxycarbonyl groups include phenoxycarbonyl and naphthoxycarbonyl. The aryloxy is linked to an adjacent moiety through the carbonyl.

"Aralkoxycarbonyl" means an aralkyl-O—C(O)— group. Non-limiting example of a suitable aralkoxycarbonyl group is benzyloxycarbonyl. The aralkoxy is linked to an adjacent moiety through the carbonyl.

"Alkylsulfonyl" means an alkyl-$S(O)_2$— group. The alkyl is linked to an adjacent moiety through the sulfonyl. Preferably, the alkyl portion of the "alkylsulfonyl" is lower alkyl.

"Alkylsulfinyl" means an alkyl-S(O)— group. The alkyl is linked to an adjacent moiety through the sulfinyl. Preferably, the alkyl portion of the "alkylsulfinyl" is lower alkyl.

"Arylsulfonyl" means an aryl-$S(O)_2$— group. The aryl is linked to an adjacent moiety through the sulfonyl.

"Aryl" means an aromatic monocyclic or multicyclic ring system comprising 6 to 14 ring carbon atoms, preferably 6 to 10 ring carbon atoms. The aryl group can be optionally substituted with one or more "ring system substituents" which may be the same or different, and are as defined herein. Non-limiting examples of suitable aryl groups include phenyl and naphthyl.

"Heteroaryl" represents cyclic aromatic groups of 5 or 6 ring atoms or bicyclic groups of 11 to 12 ring atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Preferred heteroaryls contain 5 to 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl and the like and the N-oxides thereof. Useful 5-membered heteroaryl rings include furyl, thienyl, pyrrolyl, thiazolyl, isothiazolyl, imidazolyl, pyrazolyl, isoxazolyl and the like. Useful bicyclic groups include benzo-fused ring systems derived from the heteroaryl groups named above, e.g. quinolyl, phthalazinyl, quinazolinyl, benzofuranyl, benzothienyl, indolyl and the like.

"Ring system substituent" means a substituent attached to an aromatic or non-aromatic ring system that, for example, replaces an available hydrogen on the ring system. Ring system substituents may be the same or different, each being independently selected from the group consisting of aryl, heteroaryl, aralkyl, alkylamino, arylamino, alkylaryl, heteroaralkyl, alkylheteroaryl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio and cycloalkyl.

"Cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like.

"Heterocycloalkyl" means a non-aromatic mono- or multicyclic fused ring system comprising 3 to 10 ring carbon atoms, preferably 3 to 7 ring carbon atoms, more preferably 3 to 6 ring carbon atoms, wherein the heterocycloalkyl has 1 or 2 heteroatoms independently selected from O, S or N, said heteroatom(s) interrupting a carbocyclic ring structure provided that the rings do not contain adjacent oxygen and/or sulfur atoms. The heterocycloalkylcan be optionally substituted with one or more "ring system substituents" which may be the same or different, and are as defined above.

The term "optionally substituted" means optional substitution with the specified groups, radicals or moieties.

The term "solvate" as used herein means an aggregate that consists of a solute ion or molecule with one or more solvent molecules, for example, a hydrate containing such ions.

As used herein, the terms "composition" and "formulation" are intended to encompass a product comprising the specified ingredients, as well as any product which results, directly or indirectly, from combination of the specified ingredients.

"Patient" includes both human and animals.

"Mammal" means humans and other mammalian animals.

The terms "effective amount", "therapeutically effective amount", and "pharmaceutically effective amount" are intended to mean an amount of a therapeutic agent of the compound of Formulae I, IA, IB or IC that will have an effect on a tissue, system, animal or patient that is being sought by the administrator (such as a researcher, doctor or veterinarian), which includes alleviation of the symptoms of the condition or disease being treated and the prevention, slowing or halting of progression of the disease or condition, for example, the inflammatory, immunomodulatory or respiratory diseases discussed herein.

Prodrugs and solvates of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formulae I, IA, IB and IC can form salts, solvates and prodrugs which are also within the scope of this invention. Reference to a compound of Formulae I, IA, IB or IC herein is understood to include reference to salts, solvates and prodrugs thereof, unless otherwise indicated. The term "salt(s)", as employed herein, denotes acidic salts formed with inorganic and/or organic acids, as well as basic salts formed with inorganic and/or organic bases. In addition, when a compound of Formulae I, IA, IB or IC contains both a basic moiety, such as, but not limited to, a pyridine or imidazole, and an acidic moiety, such as, but not limited to a carboxylic acid, zwitterions ("inner salts") may be formed and are included within the term "salt(s)" as used herein. Pharmaceutically effective (i.e., non-toxic, physiologically acceptable) salts are preferred, although other salts are also useful. Salts of the compounds of the formulae I, IA, IB and IC may be formed, for example, by reacting a compound of formulae I, IA, IB or IC with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; and Anderson et al, *The Practice of Medicinal Chemistry* (1996), Academic Press, New York). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quartemized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutcally acceptable salts within the scope of the invention and all acid and base salts are considered equivalent to the free forms of the corresponding compounds for purposes of the invention.

Compounds of Formulae I, IA, IB and IC, and salts and solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The present invention also relates to a pharmaceutical composition comprising one or more compounds of Formulae I, IA, IB and/or IC of this invention. Preferably, the pharmaceutical composition includes one or more pharmaceutically acceptable carriers. For preparing pharmaceutical compositions from the compounds described by this invention, inert, pharmaceutically acceptable carriers can be used. Such carriers can be either solid or liquid. Solid form preparations include powders, tablets, dispersible granules, capsules, cachets and suppositories. The powders and tablets can be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions can be found in A. Gennaro (ed.), *Remington's Pharmaceutical Sciences*, 18$^{th}$ Edition, (1990), Mack Publishing Co., Easton, Pa.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. One example includes water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations that are intended to be converted, shortly before use, to liquid form preparations for either oral or parenteral administration. Such liquid forms include solutions, suspensions and emulsions.

The compounds or compositions of the invention may also be deliverable transdermally. The transdermal compositions can take the form of creams, lotions, aerosols and/or emulsions and can be included in a transdermal patch of the matrix or reservoir type as are conventional in the art for this purpose.

Another aspect of the invention relates to a method of modulating (inhibiting or activating) a cannabinoid $CB_2$ receptor in a patient comprising administering to a patient a $CB_2$ receptor-modulating amount of one or more compounds of Formulae I, IA, IB and/or IC. The daily dose of a compound of Formulae I, IA, IB and/or IC for modulating cannabinoid $CB_2$ receptors in a patient can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day.

Another aspect of the invention relates to a method of treating cancer, inflammatory diseases, immunomodulatory diseases, or respiratory diseases comprising administering to a patient in need of such treatment one or more compounds of Formulae I, IA, IB and/or IC. Preferably, the amount of compound of Formulae I, IA, IB and/or IC administered in this aspect of the invention is a therapeutically effective amount. The daily dose of a compound of Formulae I, IA, IB and/or IC for treatment of a disease or condition can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day. For an average body weight of 70 kg, the dosage level can range from about 0.1 mg to about 700 mg of drug per day, given in a single dose or 2-4 divided doses. The exact dose, however, is determined by the attending clinician and is dependent on the potency of the compound administered, the age, weight, condition and response of the patient.

The compounds of the present invention can exhibit anti-inflammatory and/or immunomodulatory activity and are useful in the treatment of various medical conditions listed below. This utility is manifested as demonstrated by activity in the following assay.

Potential cannabinoid receptor ligands were screened for the ability to compete with [$^3$H] CP-55,940 for binding to recombinant cannabinoid receptors. Test compounds were serially diluted in Diluent Buffer (50 mM Tris pH 7.1, 1 mM EDTA, 3 mM $MgCl_2$, 0.1% BSA, 10% DMSO, 0.36% methyl cellulose (Sigma M-6385)) from stocks prepared in 100% DMSO. Aliquots (10 µl) were transferred into 96-well microtiter plates. Membrane preparations of recombinant human cannabinoid CB2 receptor (Receptor Biology #RB-HCB2) or recombinant human cannabinoid CB1 receptor (Receptor Biology #RB-HCB1) were diluted to 0.3 mg/ml in Binding Buffer (50 mM Tris pH 7.2, 1 mM EDTA, 3 mM $MgCl_2$, 0.1% BSA). Aliquots (50 µl) were added to each well of the microtiter plate. The binding reactions were initiated by addition of [$^3$H] CP-55,940 (New England Nuclear # NET 1051; specific activity=180 Ci/mmol available from New England Nuclear) to each well of the microtiter plate. Each 100 µl reaction mixture contained 0.48 nM [$^3$H] CP-55,940, 15 ug membrane protein in binding buffer containing 1% DMSO and 0.036% methyl cellulose. Following incubation for 2 hours at room temperature, the reaction mixtures were filtered through 0.5% polyethylenimine-coated GF/C filter plates (UniFilter-96, Packard) with a TomTec Mark 3U Harvester (Hamden, Conn.). The filter plate was washed 5 times with binding buffer, rotated 180°, then re-washed 5 times with binding buffer. Bound radioactivity was quantitated following addition of 30 µl of Packard Microscint 20 scintillant in a Packard TopCount NXT microplate scintillation counter. Non-linear regression analysis of the resulting data was performed using Prism 2.0b (from GraphPad, San Diego, Calif.).

The compounds of the invention exhibit potent affinities for the CB2 receptor as measured by Ki values (in nM). The activities (potencies) for the compounds of the invention are determined by measuring their Ki values. The smaller the Ki value, the more active the compound is for modulating the CB2 receptor. Compounds of the invention exhibit a wide range of activities. The CB2 average Ki values for compounds having the formulae I, IA, IB or IC generally range from >0 nM (e.g., 0.1 nM) to about 1000 nM, preferably about 0.1 nM to about 1000 nM, more preferably about 0.1 nM to about 100 nM, more preferably about 0.1 to about 20 nM, and most preferably less that about 20 nM. Representative compounds of the invention that exhibit excellent CB2 inhibitory activity ($K_i$ values of less than about 20 nanomolar, nM) are as follows: Compounds 2, 5, 6, 8, 9, 10, 12, 19, and 23 from Table 1.

The inventive compounds are also highly selective for modulating a CB2 receptor as opposed to modulating a CB1 receptor. A "selective modulator" means that a compound's selection ratio of Ki of the CB1 receptor to the Ki of the CB2 receptor is greater than about 100, preferably greater than about 500, more preferably greater than about 1000 and most preferably greater than about 3000.

It is contemplated that compounds of this invention can be useful in treating one or more of these diseases listed below.

Non-limiting examples of the cancer, inflammatory diseases, immunomodulatory diseases, and respiratory diseases include diseases selected from the group consisting of cutaneous T cell lymphoma, rheumatoid arthritis, systemic lupus erythematosus, multiple sclerosis, glaucoma, diabetes, osteoporosis, renal ischemia, myocardial infarction, cerebral stroke, cerebral ischemia, nephritis, hepatitis, glomerulonephritis, cryptogenic fibrosing aveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) and bronchitis.

Compounds of Formulae I, IA, IB and/or IC can be administered as a monotherapy. Additionally, compounds of Formulae I, IA, IB and/or IC of the present invention can be co-administered or used in combination with one or more second agents which are chemically different from the compound(s) of Formulae I, IA, IB and/or IC, for example disease-modifying antirheumatic drugs (DMARDS) such as methotrexate, azathioptrine leflunomide, penicillamine, gold salts, mycophenolate mofetil, cyclophosphamide and other similar drugs. They can also be co-administered with or used in combination with one or more non-steroidal anti-inflammatory drugs (NSAIDS) such as piroxicam, naproxen, indomethacin, ibuprofen and the like; COX-2 selective inhibitors such as rofecoxib, which is available as Vioxx® (from Merck & Company, Whitehouse Station, N.J.) and celecoxib, which is available as Celebrex® (from Pfizer Inc., New York, N.Y.); COX-1 inhibitors such as Piroxicam, which is available as Feldene® (from Pfizer Inc., New York, N.Y.); immunosuppressives such as steroids, cyclosporine, Tacrolimus, rapamycin and the like; biological response modifiers (BRMs) such as etanercept, which is available as Enbrel® (from Wyeth-Ayerst, Philadelphia, Pa.), infliximab, which is available as Remicade® (from Centocor, Inc., Malvern, Pa.), IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide, which is available as Thalomid® (Celgene Corporation, Warren, N.J.) and other small molecule inhibitors of pro-inflammatory cytokine production. Other drugs that the compounds of the invention can be co-administered or used in combination with include Anaprox, Arava, Arthrotec, Azulfidine, Aspirin, Cataflam, Celestone Soluspan, Clinoril, Cortone Acetate, Cuprimine, Daypro, Decadron, Depen, Depo-Medrol, Disalcid, Dolobid, Naprosyn, Gengraf, Hydrocortone, Imuran, Indocin, Lodine, Motrin, Myochrysine, Nalfon, Naprelan, Neoral, Orudis, Oruvail, Pediapred, Plaquenil, Prelone, Relafen, Solu-Medrol, Tolectin, Trilisate and Volataren. These include any formulation of the above named drugs.

For the treatment of multiple sclerosis, the compounds of the invention can be co-administered or used in combination or association with one or more additional agents, which may be the same or different from eachother, and are independently selected from the group consisting of Avonex® (Interferon B-1a from Biogen), Betaseron® (Interferon B-1b from Berlex) and Copaxone® (glatiramer acetate from Teva Neuroscience incorporated).

For combination treatment with more than one active agent, where the active agents are in separate dosage formulations, the active agents can be administered separately or in conjunction. In addition, the administration of one element can be prior to, concurrent to, or subsequent to the administration of the other agent, or other agents. Ideally, the active agents should be given at the same time.

Another aspect of the invention relates to a kit comprising a pharmaceutical composition for use in treating cancer, inflammatory diseases, immunomodulatory diseases, and respiratory diseases, wherein said composition comprises one or more compounds of Formulae I, IA, IB and/or IC and one or more pharmaceutically acceptable carriers. Preferably, the amount of compound(s) of Formulae I, IA, IB and/or IC in the kit is a therapeutically effective amount. The daily dose of a compound of Formulae I, IA, IB and/or IC for treatment of a disease or condition can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day.

Compounds of the present invention are generally prepared by processes known in the art, for example by the processes described below.

The following abbreviations are used in the procedures and schemes: aqueous (aq), anhydrous (anhyd), n-Butyllithium (n-BuLi), dibromodimethylhydantoin (DBDMH), diisopropylethylamine (DIPEA), diethyl ether ($Et_2O$), dimethylacetamide (DMA), dimethyl sulfoxide (DMSO), ethanol (EtOH), ethyl acetate (EtOAC), leaving group (LG), meta-chloroperoxybenzoic acid (MCPBA), methanesulfonic acid (MsOH), methanesulfnyl chloride (MsCl), preparative thin layer chromatography on Merck-silica plates (PTLC), phenyl (Ph), pyridium chlorochromate (PCC), pyridine (Py), trifluoroacetic anhyide (TFAA), triflic anhydride ($Tf_2O$), tetrahydrofuran (THF), silica gel chromatography (sgc), thin layer chromatography (TLC), room temperature (rt), hour (h), minutes (min), mole (M), pounds per square inch (psi), and saturated aqueous sodium chloride solution (brine).

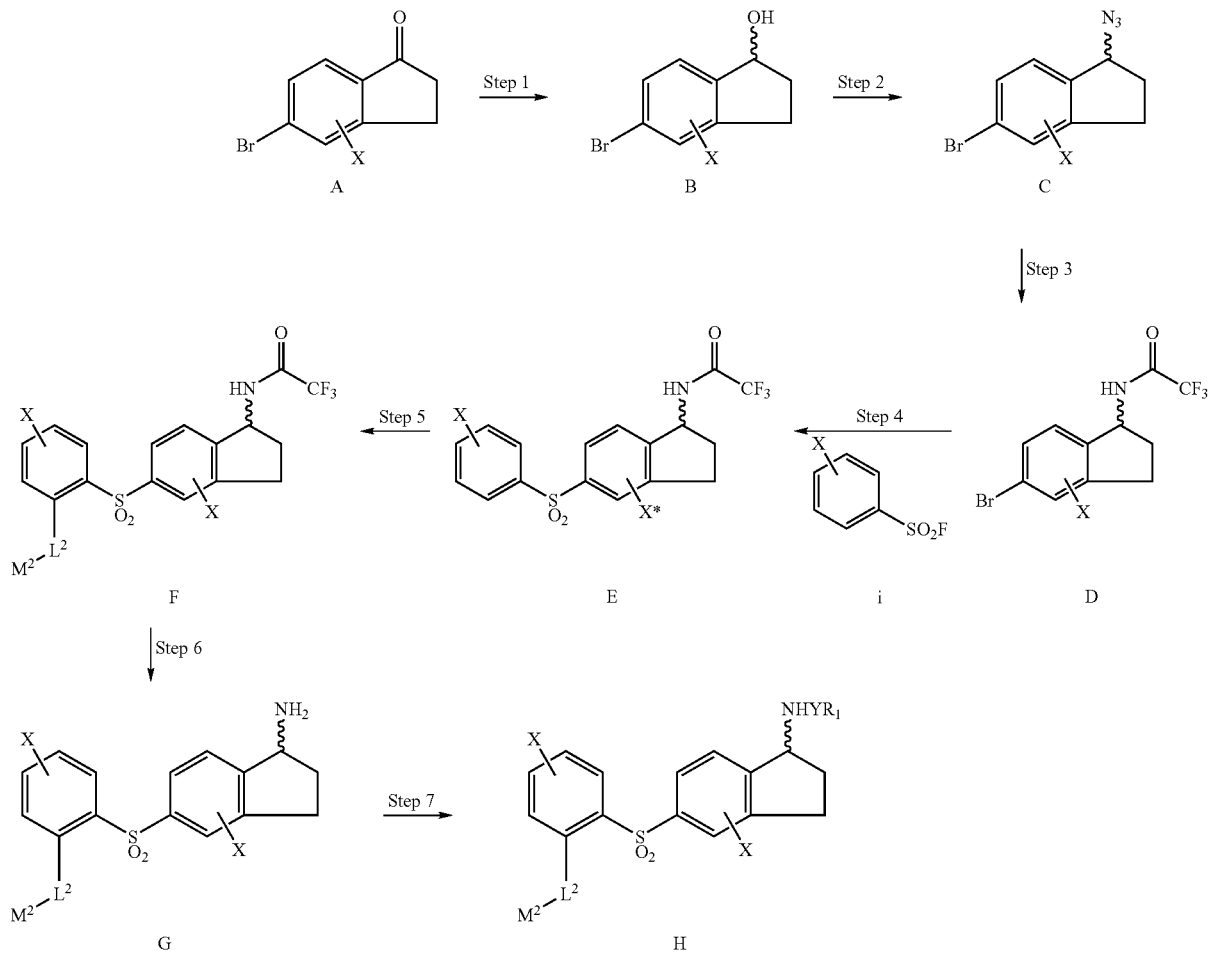

Description of Reaction General Scheme I:

In step 1, bromo indanone (compound A) is dissolved in a suitable inert solvent such as THF, methylene chloride, dicholoroethane, dioxane, or diethylether, and reacted with NaBH$_4$ at room temperature for 1-5 h to form compound B.

In step 2, compound B is dissolved in an suitable inert solvent such as toluene, benzene or toluene, and reacted with PO(OPh)$_2$N$_3$ and DBU between 0° C. and room temperature. The product (compound C) can be purified via sgc or crystallization.

In step 3, compound C is dissolved in a suitable inert solvent such as methanol, dioxane, ethanol or THF, and reacted with SnCl$_2$ between 0° C. and 45° C. for 0.5 to 48 h. The reaction mixture is then concentrated to dryness and then dissolved in a suitable inert solvent such as methylene chloride, THF, dioxane, and dichloroethane, and reacted with TFM and Et$_3$N between −78° C. and room temperature. The product (compound D) can be purified via sgc or crystallization.

In step 4, compound D is dissolved in THF or diethylether, cooled in a dry ice/IPA bath and treated with n-BuLi. The resulting anion is trapped with sulphonyl fluoride (i). The product (compound E) can be purified via chromatography or crystallization. The sulphonyl fluoride (i) is prepared by treating the corresponding sulphonyl chloride with KF in acetone and water. The sulphonyl fluoride can be purified via sgc or crystallization.

In step 5, compound E is dissolved in THF and treated with a base such as n-BuLi at −78° C. to form a dianion, which is trapped with a suitable electrophile represented by the formula M$^2$-L$^2$-LG, wherein LG represents a leaving group such as Cl, Br, mesylate or triflate. The reaction mixture is quenched with a suitable proton source such as aq NH$_4$Cl or phosphate buffer, then extracted with a suitable solvent such as EtOAc, ether, or methylacetone. The product (compound F) can be purified via sgc or crystallization.

In step 6, compound F is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred at room temperature for 0.5-24 h. The product, compound G, can be purified via sgc or rystallization.

In step 7, a combination of compound G and a tertiary amine base such as triethylamine or (iPr)$_2$NEt, is dissolved in a suitable solvent such as methylene chloride or dioxane, at room temperature, and cooled. A suitable electrophile represented by the formula R$^1$-Y-LG is added, wherein LG represents a leaving group such as bromide, chloride or fluoride. The reaction mixture is stirred between −78° C. and then at room temperature for 0.5 to 48 h. The product, compound H, can be purified via sgc or crystallization.

General Scheme II
Preparation of Benzyl amino Compounds

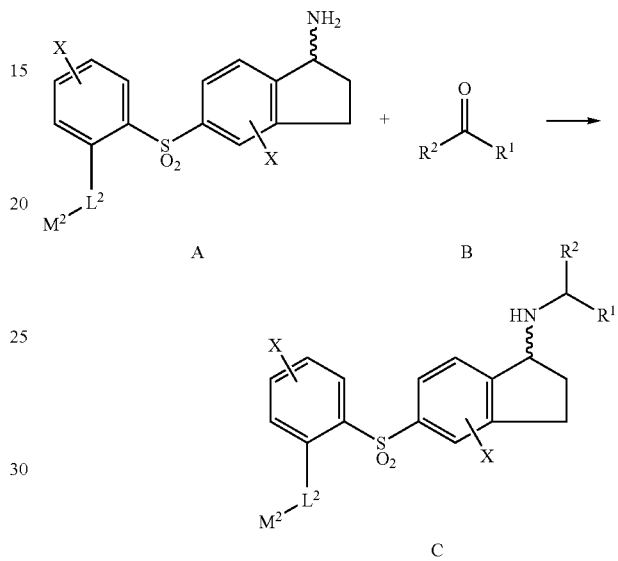

Description of Reaction General Scheme II:

The product of step 6 of Scheme I is dissolved in a suitable inert solvent such as CH$_2$Cl$_2$, THF, dioxane and dichloromethane, and reacted with a ketone or aldehyde, Na(OAc)$_3$BH and HOAc. The product can be purified via sgc or crystallization.

General Scheme III
Preparation of Indole Compounds

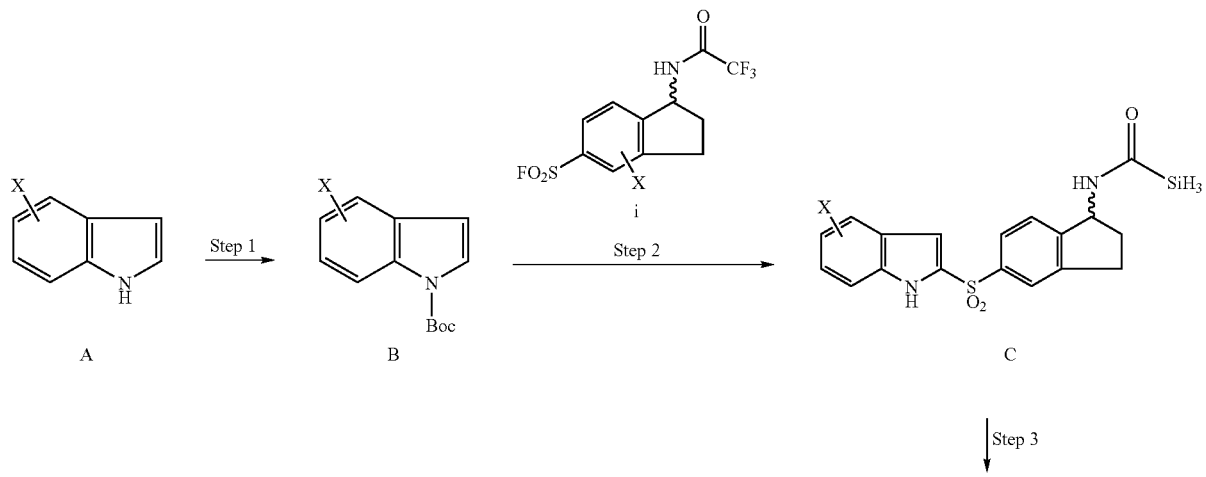

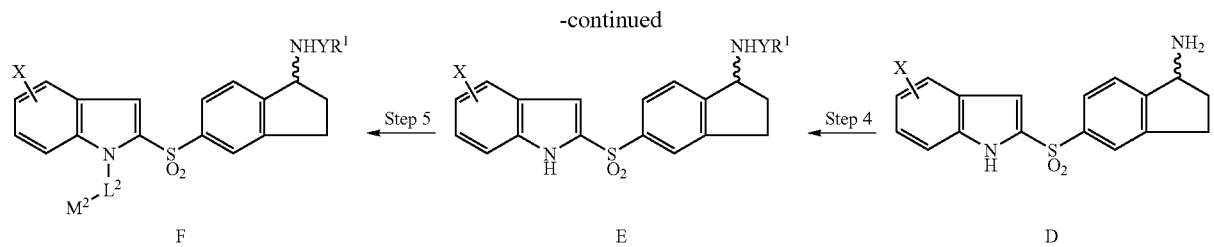

Description of Reaction General Scheme III:

In step 1, $Boc_2O$ is dissolved in a suitable inert solvent such as (THF methylene chloride or dicholoroethane, and reacted with an indole derivative, compound A, in the presence of DMAP. The product, compound B, can be purified via sgc or crystallization.

In step 2, compound B is dissolved in THF or diethylether and then cooled in a dry ice/IPA bath and treated with n-BuLi. The resulting anion is trapped with the sulphonyl fluoride (compound (i)). The product, compound C, can be purified via chromatography or crystallization. The sulphonyl fluoride (i) is prepared by dissolving the product of step 3 in Scheme I in THF or diethylether, cooled in a dry ice/IPA bath and treated with n-BuLi. The resulting anion is trapped with $SO_2$ gas followed by reacting with NCS. The resulting sulfonyl chloride is treated with KF in acetone water (1:1) solvent. The product (compound i) can be purified via chromatography or crystallization.

In step 3, compound C is dissolved in a suitable solvent such as dioxane, ethanol, methanol or THF. An alkali metal hydroxide or carbonate such as lithium hydroxide or potassium carbonate is added either as an aqueous solution or as a solid. The reaction mixture is stirred at room temperature for 0.5-24 h. The product, compound D, can be purified via sgc or crystallization.

In step 4, compound D and a tertiary amine base, such as triethylamine or $(iPr)_2NEt$, is dissolved in a suitable solvent such as methylene chloride or dioxane, at room temperature, cooled, and a suitable electrophile, which is represented by the formula $R^1$-Y-LG wherein LG can be Cl or Br is added. The reaction mixture is stirred between −78° C. and room temperature for 0.5 to 48 h. The product, compound E, can be purified via sgc or crystallization.

In step 5, compound E is dissolved in a suitable inert solvent such as THF, methylene chloride, dicholoroethane, DMF, or DMSO. Aqueous NaOH, NaOH, NaH, or $Na_2CO_3$ is used as base. An electrophile, which is represented by the formula $M^2$-$L^2$-LG, wherein LG represents a leaving group such as Cl or Br, is added and the reaction mixture is stirred in the presence of a phase-transfer catalyst, such as tetrabutyl ammonium sulfone, methyl-n-butylammonium chloride, or benzyltriethylammonium hydroxide, between 0° C. and 100° C. for 0.5 to 48 h. The product can be purified via sgc or crystallization.

General Scheme IV
Preparation of Phenyl Methylene Linked Compounds

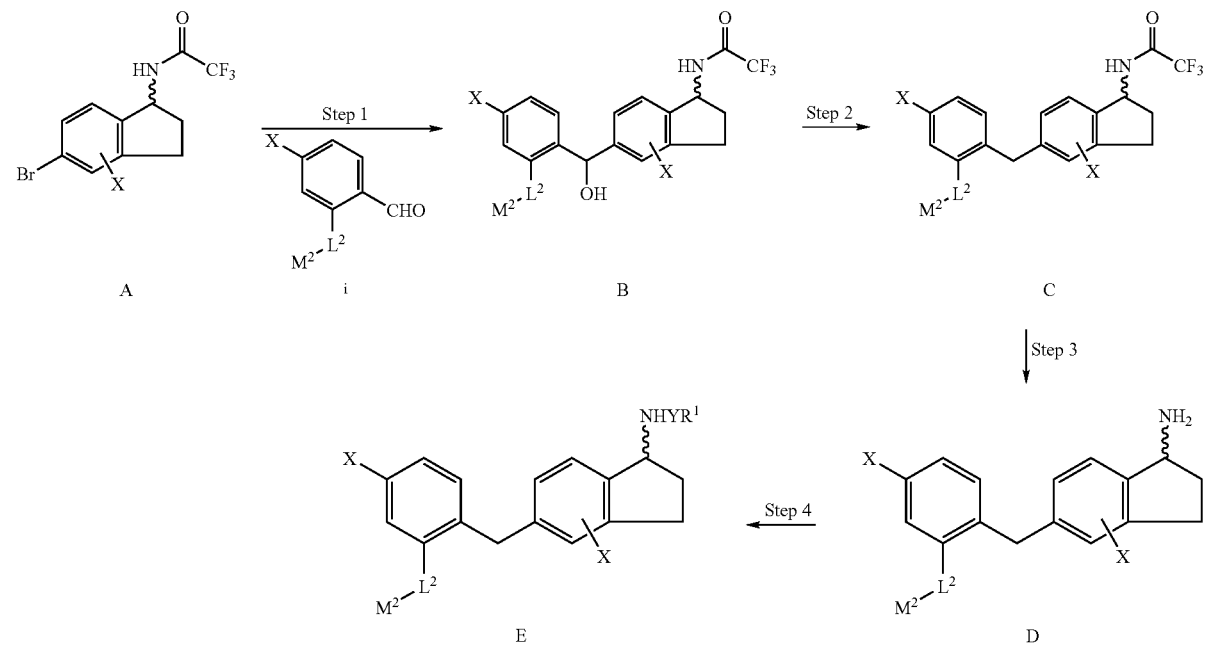

Description of Reaction General Scheme IV:

In step 1, the product of step 3 in Scheme I (compound A in Scheme 4) is dissolved in THF or diethylether, cooled in a dry ice/acetone bath (−78° C.) and treated with n-BuLi. The dianion is then treated with a THF solution diethylether containing the aldehyde (i). The resulting mixture is warmed to rt and stirred for 10 h. The product is purified (compound B) by chromotography.

The aldehyde (compound i) in step 1 was prepared by one of the following two procedures:

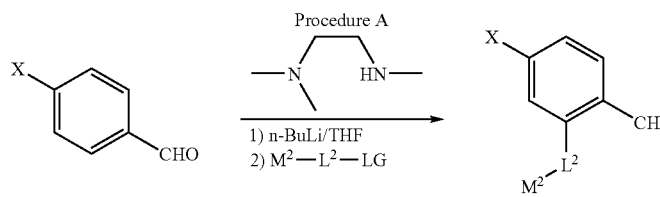

A) Regioselective ortho-lithiation of a 4-substituted benzaldehyde, and quenching with a substituted phenyl disulfide and oxidation with metachloroperoxy benzoic acid to the sulfone.
B) Base promoted displacement of fluoride from an orthofluoro benzaldehyde by a thiophenyl, phenol or aniline.

In step 2, (compound B) is dissolved in a suitable inert solvent such as THF, methylene chloride or dicholoroethane, and reacted with $Et_3SiH$ and $BF_3.Et_2O$ or trifluoroacetic acid between 0° C. and 100° C. for 0.5 to 48 h. The product (compound C) can be purified via chromatography.

In step 3 compound C is dissolved in a suitable solvent such as dioxane, ethanol, methanol or THF, and an alkali metal hydroxide or carbonate such as lithium hydroxide or potassium carbonate is added either as an aqueous solution of as a solid. The reaction mixture is stirred at room temperature for 0.5-24 h. The product, compound D, can be purified via sgc or crystallization.

In step 4, a combination of the product of step 3 and a tertiary amine base, such as triethylamine or $(iPr)_2NEt$, is dissolved in a suitable solvent, such as methylene chloride or dioxane, at room temperature, cooled, and a suitable electrophile, which is represented by the formula $R^1$—Y—LG, wherein LG is a leaving group such as Cl or Br, is added. The reaction mixture is stirred between −78° C. and room temperature for 0.5 to 48 h. The product (compound E) can be purified via sgc or crystallization.

General Scheme V
Preparation of Phenyl Carbonyl Linked Compounds

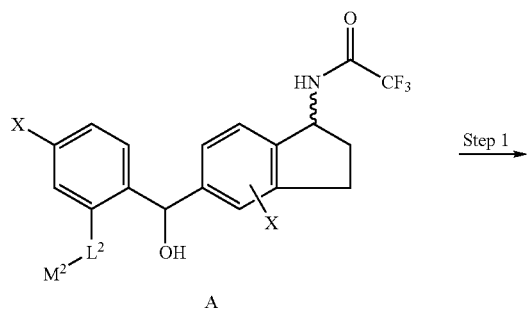

A

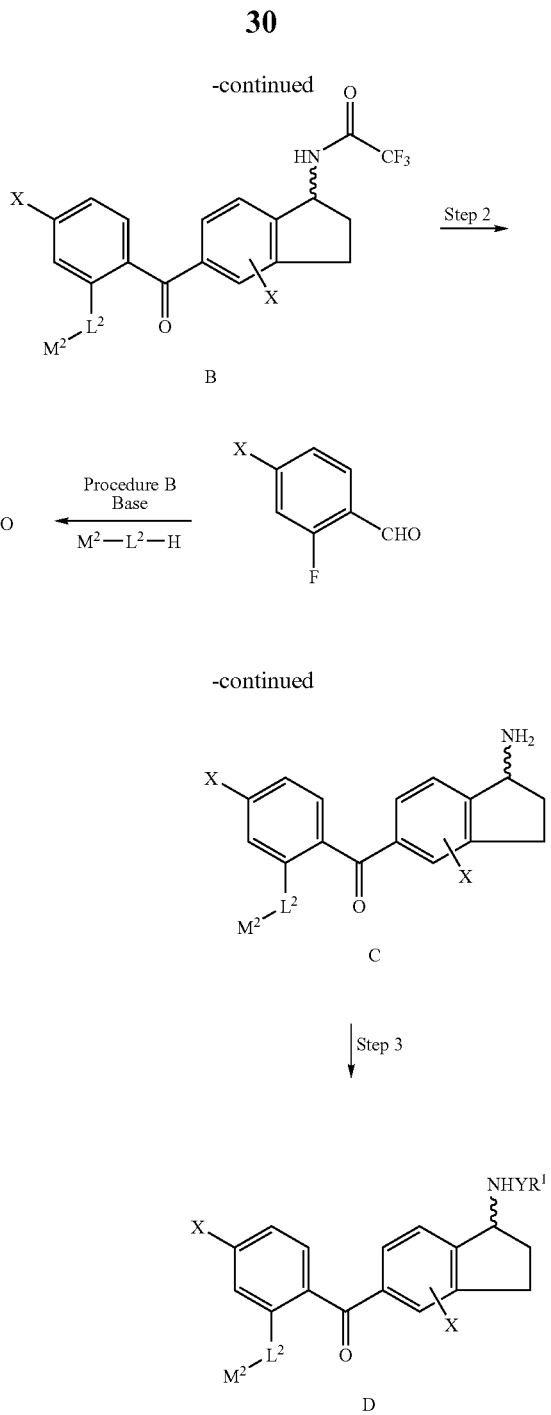

Description of Reaction General Scheme V:

In step 1, compound A (the product of step 2 in Scheme IV) is oxidized with PCC in a suitable inert solvent such as methylene chloride or dichloroethane to the ketone by stirring at rt for 18 h.

In step 2, the product of step 1 (compound B) is dissolved in a suitable solvent such as dioxane, ethanol, methanol or THF and an alkali metal hydroxide or carbonate, such as lithium hydroxide or potassium carbonate, is added either as an aqueous solution or as a solid. The reaction mixture is stirred at room temperature for 0.5-24 h. The product (compound C) can be purified via sgc or crystallization.

In step 3, a combination of compound C and a tertiary amine base, such as triethylamine or (iPr)$_2$NEt, is dissolved in a suitable solvent such as methylene chloride, dioxane, dichloroethane, or THF at room temperature, cooled, and a suitable electrophile, which is represented by the formula R$^1$—Y-LG, wherein LG represents a leaving group such as Cl, Br or F, can be added. The reaction mixture is stirred between −78° C. and room temperature for 0.5 to 48 h. The product (compound D) can be purified via sgc or crystallization.

Those skilled in the art will appreciate that similar reactions to those described in the above schemes may be carried out on other compounds of formula I as long as substituents present would not be susceptible to the reaction conditions described. Starting materials for the above processes are either commercially available, known in the art, or prepared by procedures well known in the art.

Following are examples of preparing starting materials and compounds is of Formulae I, IA, IB and/or IC. The examples are illustrative and are not intended to limit the scope of the present invention in any manner.

In the procedures, the following abbreviations are used: tetrahydrofuran (THF), trifluoroacetic acid anhydride (TFAA), 1,8-diazabicyclo[5.4.0]undec-7-ene (DBU), preparative thin layer chromatography on Merck-silica plates (PTLC), phenyl (Ph), pyridium chlorochromate (PCC), pyridine (Py), acetic acid (HOAc), n-butyl lithium (n-BuLi), meta-chloroperoxybenzoic acid (MCPBA), methane sulfonyl chloride (MsCl), triflic anyhydride (Tf$_2$O), 2-propanol (IPA), silica gel chromatography (sgc), room temperature (rt), hours (h), minutes (min), diethyl ether (Et$_2$O), anhydrous (anhyd), ethyl acetate (EtOAc), pounds per square inch (psi), and saturated sodium chloride solution (brine).

EXAMPLES

Example I

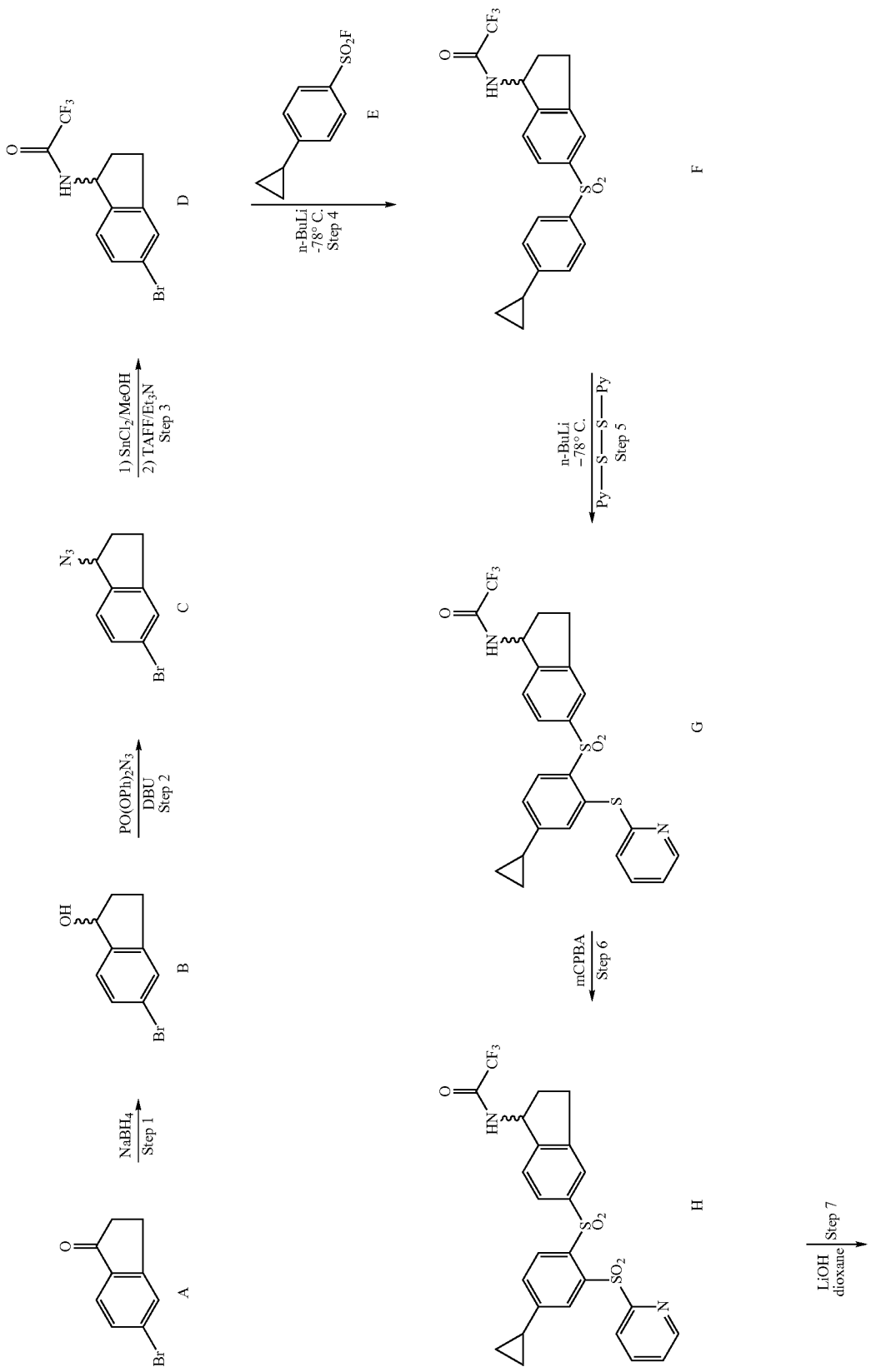

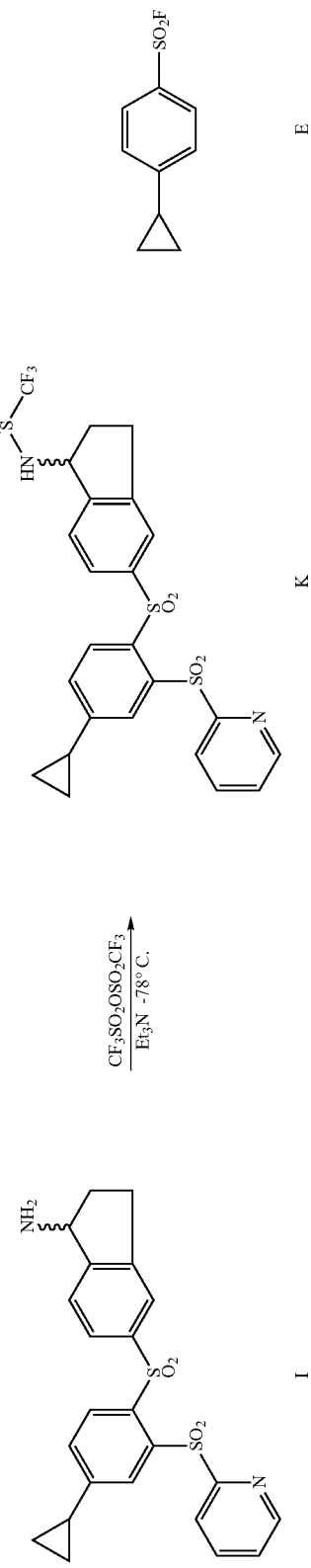
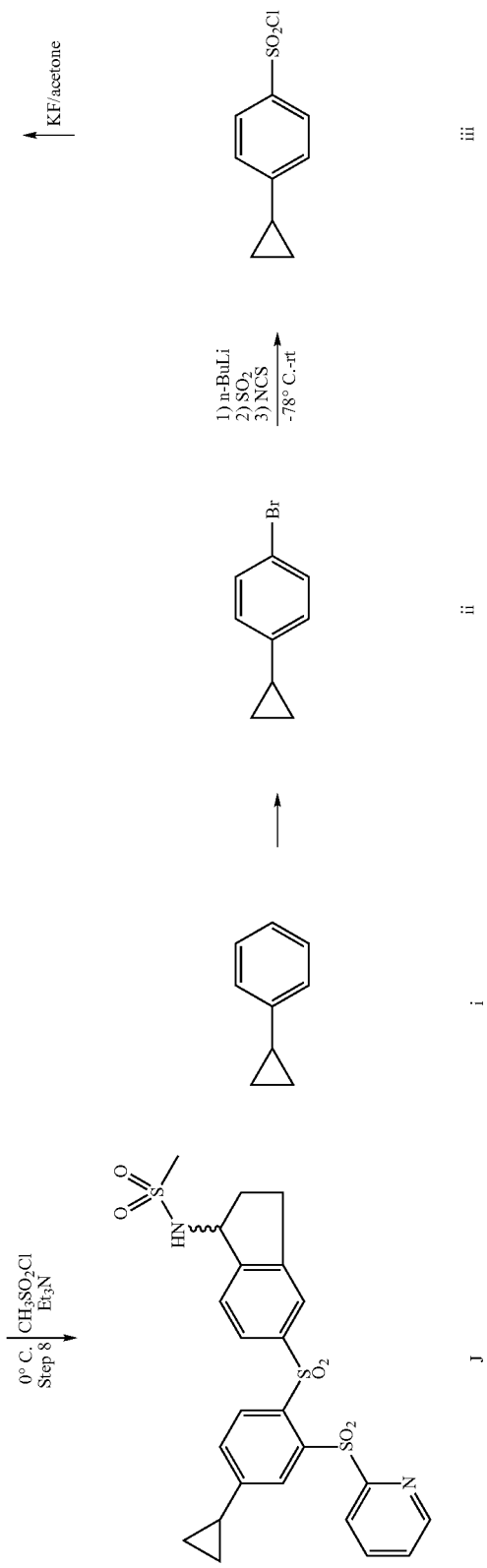

Step 1: 5-Bromo-indanone (4 g, 19 mmol) was dissolved in THF (50 mL) and MeOH (1 mL), and was reacted with $NaBH_4$ (1.4 g, 37 mmol) at rt for 1 h. EtOAc (50 mL) was added to dilute the reaction. The reaction mixture was washed with brine (80 mL). The organic layer was dried over $Na_2SO_4$ and then concentrated to dryness to give 3.9 g (97%) of compound B as a white solid.

Step 2: Compound B (3.9 g, 18.3 mmol) was dissolved in toluene (100 mL) and cooled to 0° C. $PO(OPh)_2N_3$ (5.54 mL, 25.7 mmol) and DBU (3.84 mL, 25.7 mmol) were added to the reaction mixture. The reaction was slowly brought up to rt and stirred for 3 h. EtOAc (50 mL) was added to dilute the reaction. The reaction mixture was washed with $H_2O$ (100 mL×3). The organic layer was dried over $Na_2SO_4$ and then concentrated to dryness. The crude product was purified via sgc (hexanes) to give 4.12 g (94%) of compound C as a light brown oil.

Step 3: Compound C (2.5 g, 10.5 mmol) was dissolved in MeOH (40 mL) and reacted with $SnCl_2.2H_2O$ (4.7 g, 20.8 mmol) at rt overnight. The solvent was removed and NaOH (aq, 1 N, 50 mL) was added. The reaction mixture was extracted into EtOAc (50 mL). The organic layer was extracted with HCl (1N, 50 mL×2) and the aquoues layer was basified with solid NaOH until the pH was about 11. The mixture was extracted with EtOAc (50 mL×3). The organic layers were combined and dried over $Na_2SO_4$ and then concentrated to give the corresponding amine. The amine was dissolved in $CH_2Cl_2$ (50 mL) and cooled to −78° C. TFAA (1.47 g, 6.9 mmoL) was added followed by slow addition of $Et_3N$ (1.05 g, 10.4 mmol). The reaction mixture was slowly warmed up to rt and stirred for 3 h. $H_2O$ (50 mL) was used to wash the reaction mixture. The organic layer was washed with brine, then dried over $Na_2SO_4$, and concentrated to dryness. The crude product was purified via sgc (25% EtOAc/hexanes) to give 3.1 g (96%) of compound D.

Step 4: In a flame dried flask under $N_2$ blanket, compound D (1.5 g, 4.9 mmol) was dissolved in dry THF (30 mL) and cooled to −78° C. n-Butyl lithium (1.9 M in hexanes, 5.4 mL, 9.7 mmol) was added followed after 45 min by compound E (1.27 g, 6.3 mmol). The cold bath was removed after 2 h and the reaction mixture was allowed to warm to rt over 45 minutes then quenched with aq$NH_4Cl$. EtOAc (30 mL) was added to dilute the reaction mixture. The reaction mixture was washed with brine (100 mL×2). The organic layer was dried over $Na_2SO_4$ and then concentrated to dryness. The crude material was purified via sgc (25% EtOAc/Hexanes) to give 545 mg (27%) of compound F.

Compound i (120 g, 1.0 mml) was dissolved in $CH_2Cl_2$ (1.2 L) with $Hg_2O$ (6.0 g, 14.4 mmol) and $K_2CO_3$ (24.0 g, 0.17 mol) and cooled to −30° C. $Br_2$ (85.2 g, 1.1 mol) was added over 10 min period of time. The reaction mixture was stirred at −30° C. for 4.5 h. The reaction mixture was washed with $H_2O$ (1 L) and brine (1 L). The organic layer was dried over $Na_2SO_4$ and concentrated to dryness. The crude material was distilled under reduced pressure to give 103.8 g (52%) of compound ii.

In a flame dried flask under $N_2$ blanket, compound ii (6.0 g, 30.5 mmol) was dissolved in dry THF (30 mL) and cooled to −78° C. A solution of n-butyl lithium (1.75 M in hexanes, 17.4 mL, 30.5 mmol) was added and the reaction mixture was stirred for 20 min. $SO_2$ was bubbled in the reaction for 20 min. It was slowly warmed up to rt. $CH_2Cl_2$ (50 mL) was added and the mixture was reacted with NCS (5.0 g, 37.4 mmol) at rt overnight. The reaction mixture was washed with brine (100 mL×2). The organic layer was dried over $Na_2SO_4$ and then concentrated to dryness. The crude material was purified via sgc (5% EtOAC/Hexanes) to give 3.65 g (55%) of compound ii.

To a round-bottom flask was added compound iii (3.0 g, 13.8 mmol) and KF (2.4 g, 41.4 mmol) followed by addition of acetone (50 mL) and water (30 mL). The reaction mixture was stirred at room temperature overnight. The solvent was then removed. Methylene chloride (40 mL) was added and it was washed with brine (40 mL). The organic layer was dried over $Na_2SO_4$ and then concentrated to dryness to give 2.77 g (100%) of compound E.

Step 5. In a flame dried flask under $N_2$ blanket, compound F (545 mg, 1.3 mmol) was dissolved in anhyd THF (20 mL) and cooled to −78° C. A solution of n-butyl lithium (1.8 M in hexanes, 1.5 mL, 2.7 mmol) was added and the reaction mixture was stirred for 40 min. 2-2'-dithiodipyridine (352 mg, 1.6 mmol) was added and the reaction mixture was stirred at −78° C. for 3 h before slowly warmed up to rt. The reaction mixture was then quenched with aq $NH_4Cl$. The reaction mixture was partitioned between EtOAc and water. The auqueous layer was extracted with additional EtOAc. The combined organic layers were washed with aq $Na_2CO_3$ and brine, then dried with $Na_2SO_4$ and concentrated to dryness. The crude product was purified via sgc (33% EtOAc/Hexanes) to give 358 mg (52%) of compound G.

Step 6: Compound G (358 mg, 0.69 mmol) was dissolved in $CH_2Cl_2$ (30 mL) and cooled to 0° C. MCPBA (430 m g, ca 1.7 mmol) was added. The ice bath was removed and the reaction mixture was stirred at rt overnight. Aqueous $NaHCO_3$ (200 mL) and $CH_2Cl_2$ were added and the layers were separated. The organic layer was washed with aq $NaHSO_3$, $NaHCO_3$, $H_2O$, and brine and then dried with $Na_2SO_4$. The crude product was purified by sgc (33% EtOAc/hexanes) to give 245 mg (64%) of compound H.

Step 7: Compound H (245 mg, 0.44 mmol) was dissolved in dioxane (8 mL) at room temperature. LiOH (1.0 M, 8.0 mL, 8.0 mmol) was added and the mixture was stirred at room temperature overnight. The solvent was removed and $CH_2Cl_2$ (15 mL) and brine (15 mL) was added and the layers were separated. The aqueous layer was extracted with additional $CH_2Cl_2$ (15 mL) and the combined organic layers were dried over $Na_2SO_4$ and concentrated to dryness to give compound I 180 mg (89%).

Step 8: Compound I (100 mg, 0.22 mmol) was dissolved in $CH_2Cl_2$ (10 mL) and cooled to 0° C. Methanesulfonyl chloride (33 mg, 0.29 mmol) was added followed by addition of triethylamine (33 mg, 0.33 mmol). The reaction mixture was slowly warmed up to room temperature and stirred for 1 h. Brine (15 mL) was added and extracted. The organic layer was dried over $Na_2SO_4$ and concentrated to dryness. The crude product was purified via PTLC (50% EtOAc/hexanes) to give 109 mg (93%) of compound J.

Step 9. Compound H (20 mg, 0.044 mmol was dissolved in $CH_2Cl_2$ (15 mL) and cooled to −78° C. $Et_3N$ (7 mg, 0.069 mmol) was added followed by the addition of trifluoromethanesulfonic anhydride (15 mg, 0.053 mmol). The reaction mixture was stirred for 30 min before warming up to 0° C. Brine (15 mL) was added and the product was extracted with $CH_2Cl_2$ (50 mL). The organic layer was dried over $Na_2SO_4$ and concentrated to dryness. The crude product was purified via PTLC (33% EtOAc/hexanes) to give 26 mg (100%) compound K.

Example II

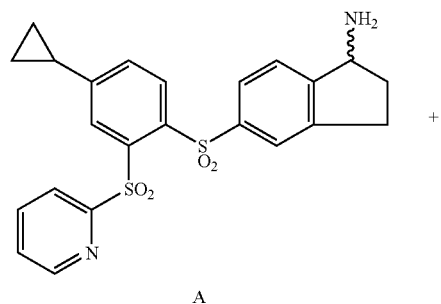

A

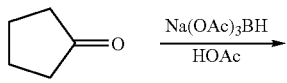

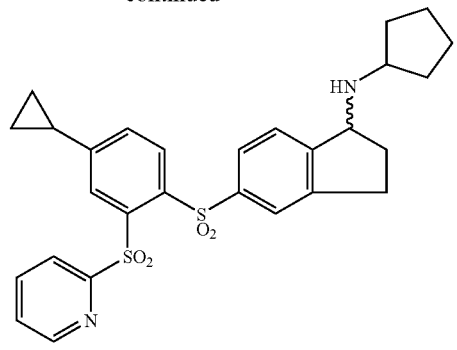

B

Compound A (prepared in step 7 of Example 1) (20 mg, 44 μmol) was dissolved in $CH_2Cl_2$ (10 mL) at rt. $Na(OAc)_3BH$ (14 mg, 66 μmol) was added followed by addition of acetic acid (3 mg, 44 μmol). The reaction mixture was stirred at rt overnight. Brine (15 mL) was added and extracted. The organic layer was dried over $Na_2SO_4$ and concentrated to dryness. The crude product was purified via PTLC (EtOAc) to give 23 mg (99%) of compound B.

Example III

Description of Reaction-Example III

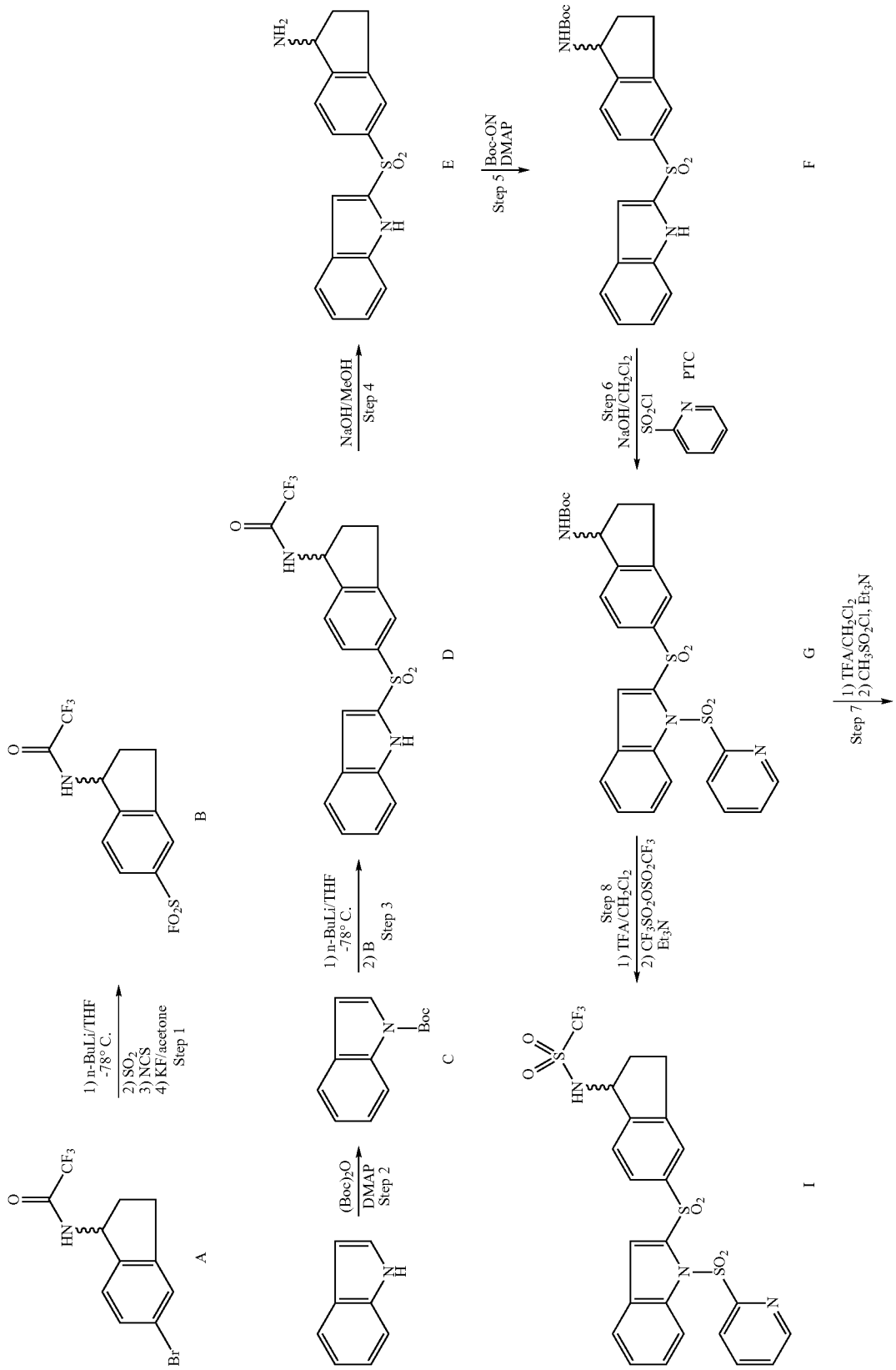

-continued
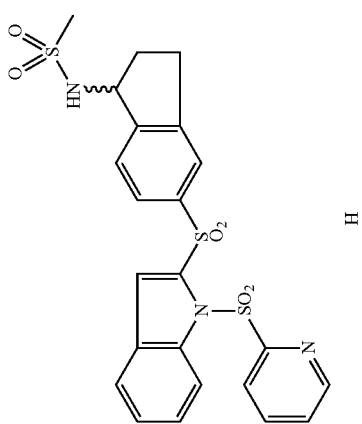

Step 2: Indole (10 g, 85 mmol) was dissolved in methylene chloride (200 mL). $Boc_2O$ (20 g, 92 mmol) and DMAP (cat.) were added and the reaction was stirred at room temperature overnight. The reaction mixture was washed with brine (100 mL). The organic layer was dried over $Na_2SO_4$, and concentrated to dryness. The crude product was purified via sgc (25% EtOAc/hexanes) to give 18.6 g (100%) of compound C.

Step 1: In a flame dried flask under $N_2$ blanket, compound A (3.1 g, 1 0.0 mmol) was dissolved in dry THF (30 mL) and cooled to −78° C. A solution of n-butyl lithium (2.0 M in hexanes, 10 mL, 20.0 mmol) was added and the reaction mixture was stirred for 20 min. $SO_2$ was bubbled in the is reaction for 20 min. The reaction mixture was slowly warmed upto rt. $CH_2Cl_2$ (50 mL) was added and the mixture was reacted with NCS (2.7 g, 20.2 mmol) at rt overnight. The reaction mixture was washed with brine (100 mL×2). The organic layer was dried over $Na_2SO_4$ and then concentrated to dryness. The crude material was purified via sgc (25% EtOAC/Hexanes) to give the corresponding sulphonyl chloride compound (1.4 g). This material was dissolved in acetone (50 mL). KF (1.2 g, 20.7 mmol) was added followed by addition of water (30 mL). The reaction mixture was stirred at room temperature overnight. The solvent was then removed. Methylene chloride (40 mL) was added and it was washed with brine (40 mL). The organic layer was dried over $Na_2SO_4$ and then concentrated to dryness to give 1.24 g (39%) of compound B.

Step 3: In a flame dried flask under $N_2$ blanket, compound 1 (565 mg, 2.6 mmol) was dissolved in dry THF (20 mL) and cooled to −78° C. A solution of n-butyl lithium (1.9 M in hexanes, 1.37 mL, 2.6 mmol) was added and the reaction mixture was stirred for 45 min. Compound 3 (270 mg, 0.87 mmol) in THF (1.5 mL) was added and the reaction mixture was stirred at −78° C. for several hours and then slowly warmed up to room temperature. The reaction mixture was stirred at room temperature for 1 day. The reaction mixture was then quenched with saturated aqueous $NH_4Cl$ (20 mL). Ethyl acetate (30 mL) was added and the layers were separated. The organic layer was washed with brine, then dried over $Na_2SO_4$, and concentrated to dryness. The crude product was purified via sgc (25% EtOAc/hexanes) to give 67 mg (19%) of compound D.

Step 4: Compound D (63 mg, 0.15 mmol) was dissolved in methanol (2 mL) at room temperature. NaOH (1.0 M, 0.90 mL, 0.90 mmol) was added and the mixture was stirred at room temperature for 3 h. The solvent was removed and $CH_2Cl_2$ (15 mL) and brine (15 mL) was added and the layers were separated. The aqueous layer was extracted with additional $CH_2Cl_2$ (15 mL) and the combined organic layers were dried over $Na_2SO_4$ and concentrated to dryness to give compound E (48 mg, 99%).

Step 5: Compound E (48 mg, 0.15 mmol) was dissolved in $CH_2Cl_2$ (10 mL). Boc-ON (38 mg, 0.15 mmol) was added followed by addition of DMAP (cat). The reaction mixture was stirred at room temperature overnight. Brine (15 mL) was added and extracted. The organic layer was dried over $Na_2SO_4$ and concentrated to dryness. The crude product was purified via PTLC (25% EtOAc/hexanes) to give 56 mg (88%) compound F.

Step 6: Compound F (50 mg, 0.12 mmol) was dissolved in $CH_2Cl_2$ (5 mL). NaOH (1.0 M, 1.5 mL) was added followed by addition of 2-pyridine sulphonyl chloride (48 mg, 0.27 mmol), and tetrabutylammonium hydrogensulfate (cat.). The reaction mixture was stirred at room temperature overnight. The aqueous layer was then removed, and the organic layer was dried over $Na_2SO_4$ and concentrated to dryness. The crude product was purified via PTLC (25% EtOAc/hexanes) to give 54 mg (81%) of compound G.

Step 7: Compound G (37 mg, 0.067 mmol) was stirred with $TFA:CH_2Cl_2$ (1:3, 10 mL) at rt for 2 h. The reaction mixture was concentrated to dryness and was further dried under vacuum. This material was dissolved in $CH_2Cl_2$ (10 mL) and cooled to 0° C. Methanesulfonyl chloride (12 mg, 0.10 mmol) was added followed by addition of triethylamine (20 mg, 0.20 mmol). The reaction mixture Was slowly warmed up to room temperature and stirred overnight. Brine (15 mL) was added and extracted. The organic layer was dried over $Na_2SO_4$ and concentrated to dryness. The crude product was purified via PTLC (50% EtOActhexanes) to give 23 mg (66%) of compound H.

Step 8: Compound G (37 mg, 0.067 mmol) was stirred with $TFA:CH_2Cl_2$ (1:3, 10 mL) at rt for 2 h. The reaction mixture was concentrated to dryness and was further dried under vacuum. This material was dissolved in $CH_2Cl_2$ (15 mL) and cooled to −78° C. $Et_3N$ (20 mg, 0.20 mmol) was added followed by the addition of trifluoromethanesulfonic anhydride (23 mg, 0.08 mmol). The reaction mixture was stirred for 30 min before warming up to 0° C. Brine (15 mL) was added and the product was extracted with $CH_2Cl_2$ (50 mL). The organic layer was dried over $Na_2SO_4$ and concentrated to dryness. The crude product was purified via PTLC (25% EtOAc/hexanes) to give 13 mg (40%) compound I.

Example IV

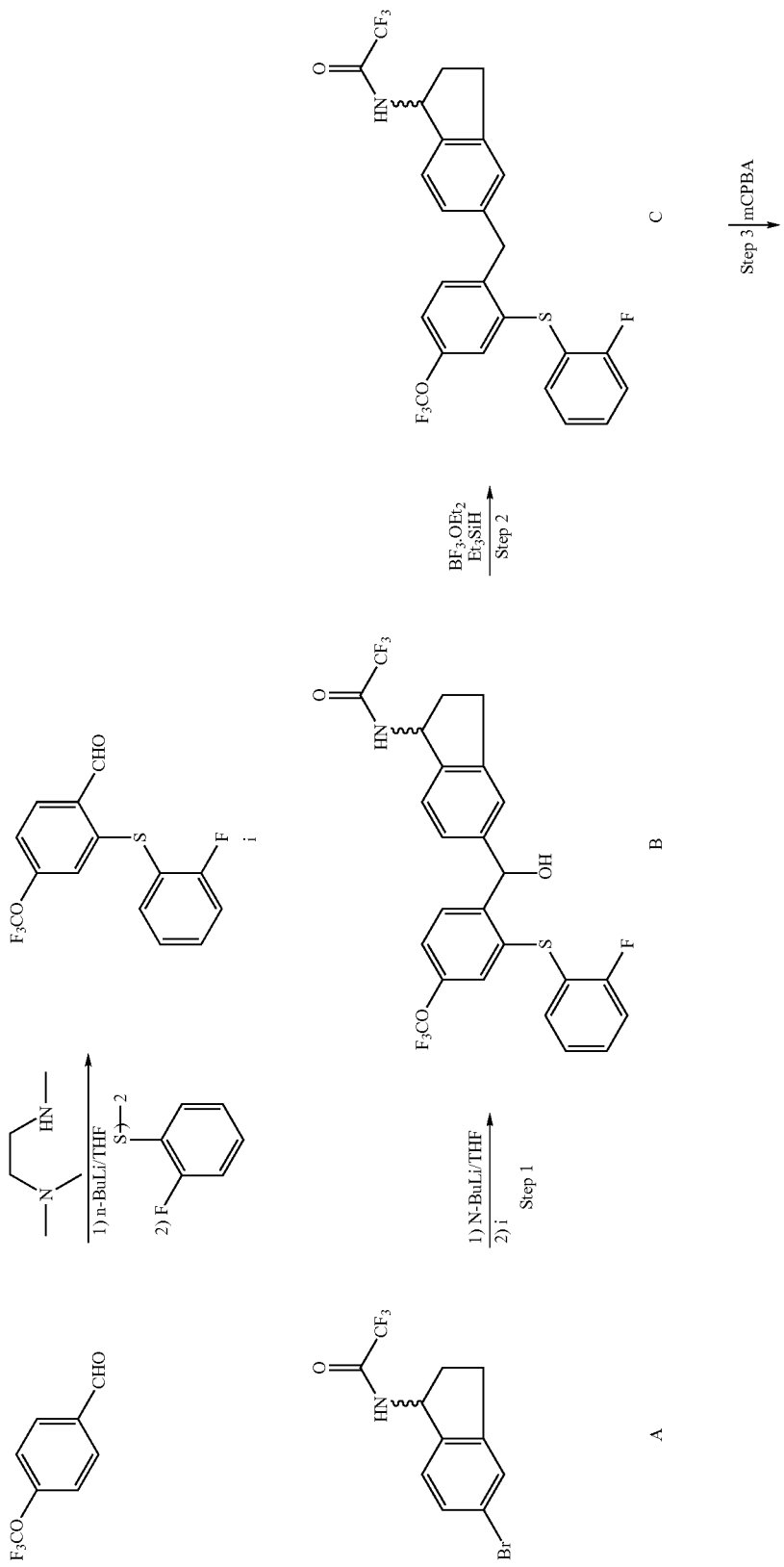

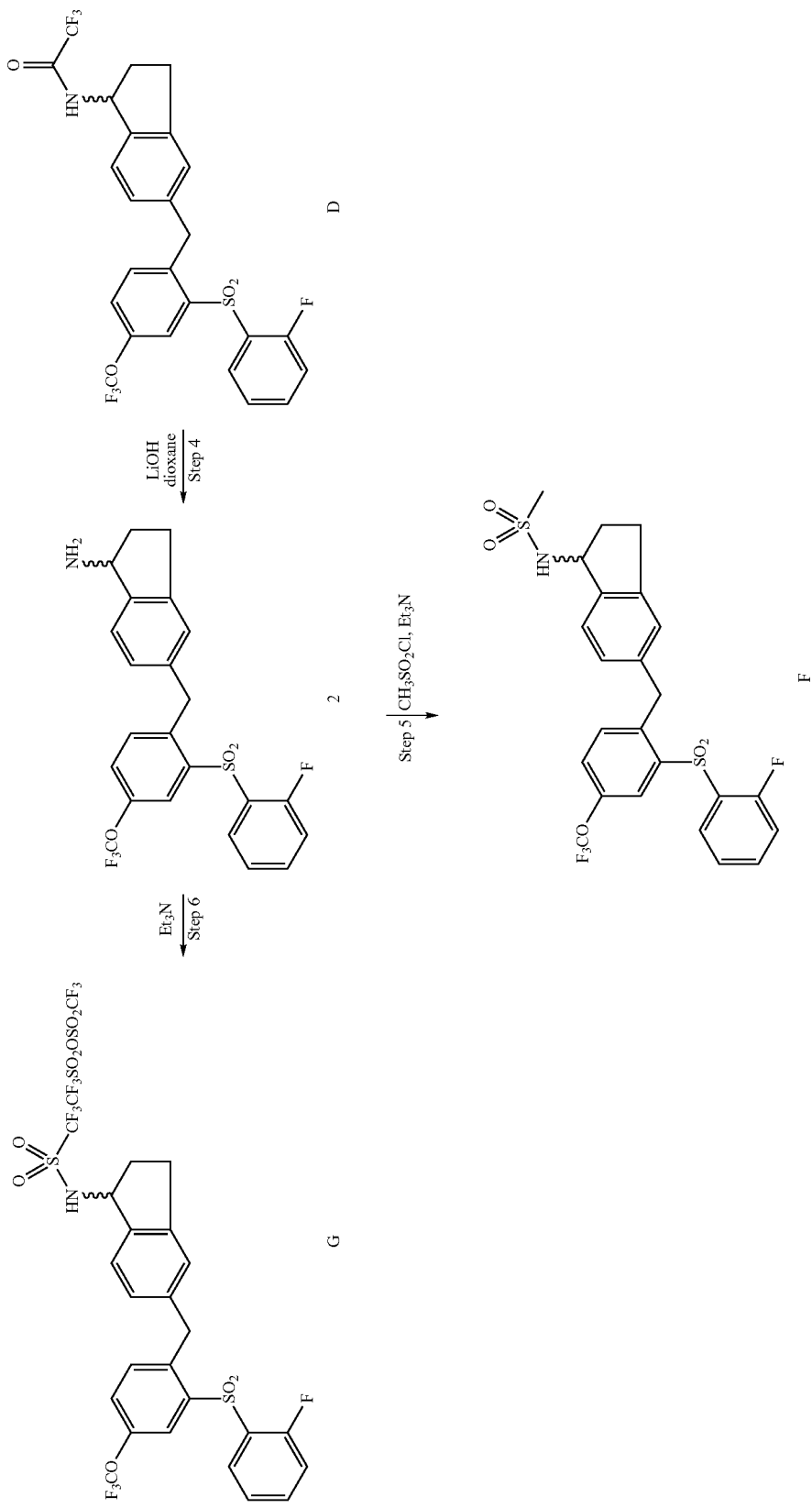

Step 1: In a flame dried flask under $N_2$ blanket, compound A (325 mg, 1.0 mmol) was dissolved in dry THF (20 mL) and cooled to −78° C. A solution of n-butyl lithium (1.78 M in hexanes,1.24 mL, 2.2.mmol) was added and the reaction mixture was stirred for 45 min. Compound i (333 mg, 1.0 mmol) in THF (1.5 mL) was added and the reaction mixture was stirred at −78° C. for several hours before slowly warmed up to room temperature. The reaction mixture was then quenched with saturated aqueous $NH_4Cl$ (20 mL). Ethyl acetate (30 mL) was added and the layers were separated. The organic layer was washed with brine, dried over $Na_2SO_4$, and then concentrated to dryness. The crude product was purified via sgc (25% EtOAc/hexanes) to give 235 mg (41%) of compound B.

Preparation of aldehyde i: To a solution of N,N, N'-Trimethylethylenediamine (1.2 mL, 8. 6 mmoles) in THF (8 mL) at −20° C. was added n-BuLi (1.6 M, 5.4 mL, 8.6 mmoles) dropwise. After 15 minutes 4-trifluoromethoxybenzaldehyde (1.5 g, 7.8 mmoles) in THF (8 mL) was added. The mixture was stirred for 15 minutes and more of n-BuLi (1.6M, 14.6 mL, 23 mmole) was added. The reaction mixture was stirred at −20° C. for 1 h, then placed in the freezer at −20° C. for 20 h. The mixture was cooled to −40° C., followed by addition of solution of o-fluorobenzenedisulfide (4.0 g, 15.7 mmoles) in 30 mL THF and stirred at −40° C. to −35° C. for 3 h. The reaction was poured into 0.5 N HCl and extracted with ethyl acetate.The organic layer was washed with water and brine and then dried over $Na_2SO_4$, filtered and concentrated to give yellow oil. It was purified by silica-gel column chromatography (3% ethylacetate/hexanes) to give light yellow solid 1.55 g (62%).

Step 2: Compound B (140 mg, 0.26 mmol) was dissolved in $CH_2Cl_2$ (10 mL). Triethylsilane (0.17 mL, 1.0 mmol) was added followed by addition of $BF_3$.EtOEt (0.13 mL, 1.0 mmol). The reaction mixture was then stirred at room temperature overnight. After removing the solvent, the crude product was purified via PTLC (20% EtOAc/hexanes) to give 90 mg (66%) compound C.

Step 3: Compound C (36 mg, 0.068 mmol) was dissolved in $CH_2Cl_2$ (1 mL) and cooled to 0° C. MCPBA (70 m g, ca 0.29 mmol) was added. The ice bath was removed and the reaction mixture was stirred at rt overnight. Aqueous $NaHCO_3$ (200 mL) and $CH_2Cl_2$ were added and the layers were separated. The organic layer was washed with aq $NaHSO_3$, $NaHCO_3$, $H_2O$, and brine then dried with $Na_2SO_4$. The crude product was purified by sgc (33% EtOAc/hexanes) to give 23 mg (61%) of compound D.

Step 4: Compound D (20 mg, 0.036 mmol) was dissolved in dioxane (2 mL) at room temperature. LiOH (1.0 M, 1 mL, 1.0 mmol) was added and the mixture was stirred at room temperature overnight. The solvent was removed and $CH_2Cl_2$ (15 mL) and brine (15 mL) were added and the layers were separated. The aqueous layer was extracted with additional $CH_2Cl_2$ (15 mL) and the combined organic layers were dried over $Na_2SO_4$ and concentrated to dryness to give 14 mg (83%) of compound E.

Step 5: Compound E (24 mg, 0.052 mmol) was dissolved in $CH_2Cl_2$ (10 mL) and cooled to 0° C. Methanesulfonyl chloride (6 mg, 0.052 mmol) was added followed by addition of $Et_3N$ (13 mg, 0.13 mmol). The reaction mixture was slowly warmed up to room temperature and stirred overnight. Brine (15 mL) was added and extracted. The organic layer was dried over $Na_2SO_4$ and concentrated to dryness. The crude product was purified via PTLC (33% EtOAc/ hexanes) to give 15 mg (54%) of compound F.

Step 6: Compound E (42 mg, 0.09 mmol) was dissolved in $CH_2Cl_2$ (5 mL) and cooled to −78° C. $Et_3N$ (23 mg, 0.23 mmol) was added followed by the addition of trifluoromethanesulfonic anhydride (25 mg, 0.09 mmol). The reaction mixture was stirred for 2 h before warming up to 0° C. Brine (15 mL) was added and the product was extracted with $CH_2Cl_2$ (50 mL). The organic layer was dried over $Na_2SO_4$ and concentrated to dryness. The crude product was purified via PTLC (33% EtOAc/hexanes) to give 22 mg (40%) compound G.

Example V

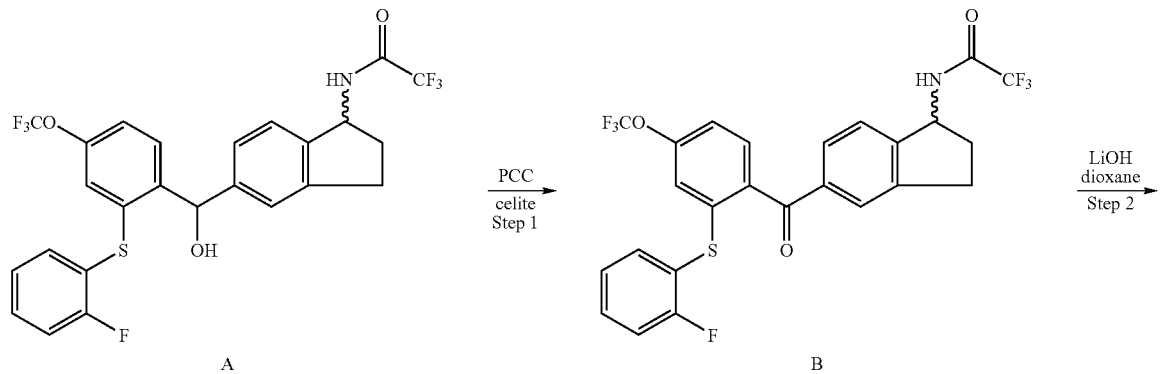

-continued

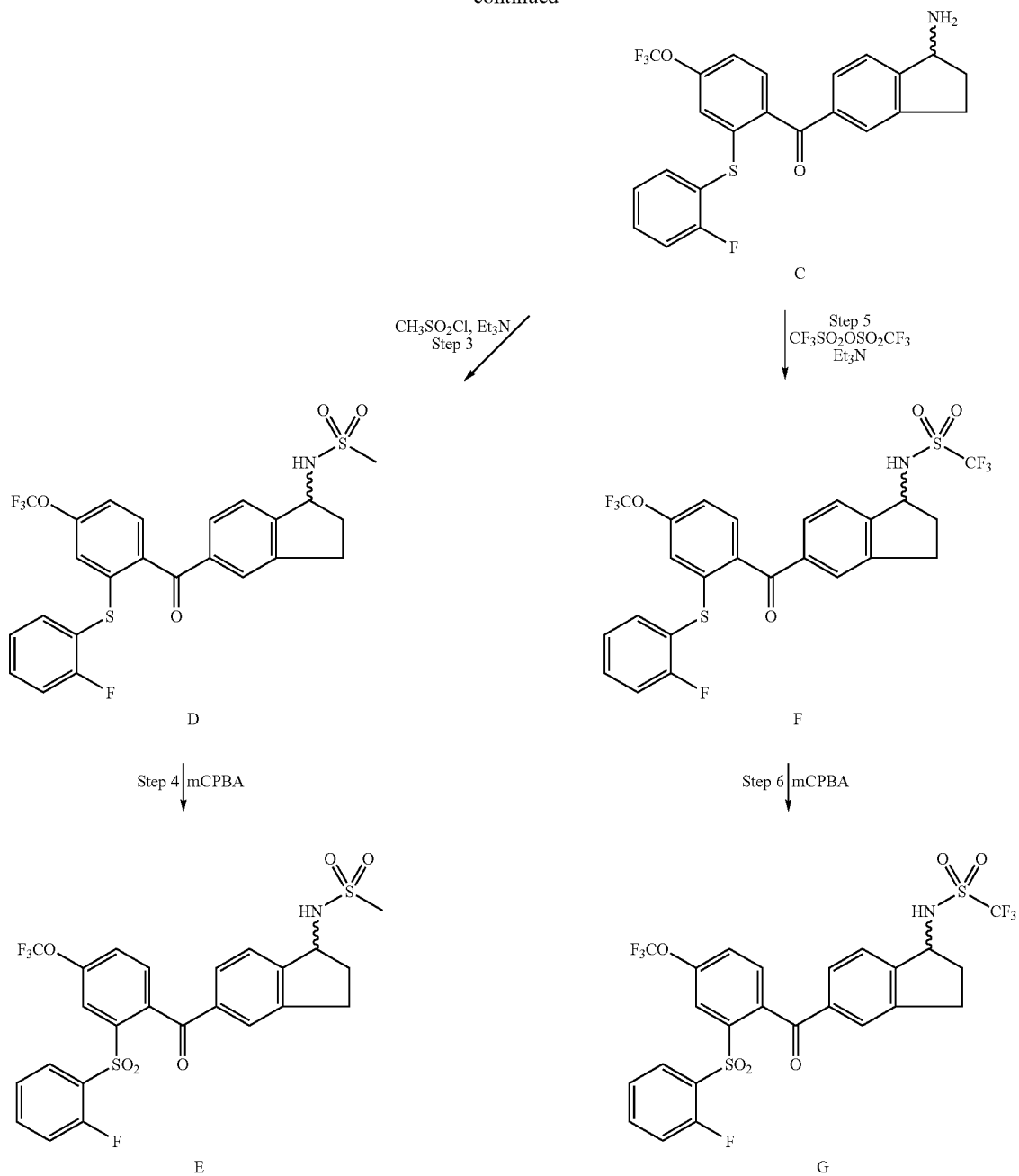

Step 1. Compound A (94 mg, 0.17 mmol), which was prepared in Example 4, Step 1, was dissolved in CH$_2$Cl$_2$ (20 mL) at room temperature. Celite (90 mg) was added followed by addition of PCC (94 mg, 0.43 mmol). The mixture was stirred at room temperature overnight. The solid was filtered off and the organic layer was washed with NaHCO$_3$ and brine. The organic layer was dried over Na$_2$SO$_4$ and concentrated to dryness. The crude product was purified via PTLC (20% EtOAc/hexanes) to give 76 mg (81%) of compound B.

Step 2: Compound B (76 mg, 0.14 mmol) was dissolved in dioxane (3 mL) at room temperature. LiOH (1.0 M, 1 mL,  1.0 mmol) was added and the mixture was stirred at room temperature overnight. The solvent was removed and CH$_2$Cl$_2$ (15 mL) and brine (15 mL) was added and the layers were separated. The aqueous layer was extracted with additional CH$_2$Cl$_2$ (15 mL) and the combined organic layers were dried over Na$_2$SO$_4$ and concentrated to dryness to give 56 mg (89%) of compound C.

Step 3: Compound C (27 mg, 0.06 mmol) was dissolved in CH$_2$Cl$_2$ (10 mL) and cooled to 0° C. Methanesulfonyl chloride (7 mg, 0.06 mmol) was added followed by addition of Et$_3$N (15 mg, 0.15 mmol). The reaction mixture was slowly warmed up to room temperature and stirred overnight. Brine (15 mL) was added and extracted. The organic layer was dried over Na$_2$SO$_4$ and concentrated to dryness. The crude product was purified via PTLC (33% EtOAc/hexanes) to give 17 mg (54%) of compound D.

Step 4: Compound D (15 mg, 0.028 mmol) was dissolved in CH$_2$Cl$_2$ (1 mL) and cooled to 0° C. MCPBA (31 mg, ca 0.1 mmol) was added. The ice bath was removed and the reaction mixture was stirred at rt overnight. Aqueous NaHCO$_3$ (200 mL) and CH$_2$Cl$_2$ were added and the layers were separated. The organic layer was washed with aq NaHSO$_3$, NaHCO$_3$, H$_2$O, and brine then dried with Na$_2$SO$_4$. The crude product is purified via PTLC (50% EtOAc/hexanes) to give 10 mg (63%) of compound E.

Step 5: Compound E (28 mg, 0.06 mmol) was dissolved in CH$_2$Cl$_2$ (5 mL) and cooled to −78° C. Et$_3$N (15 mg, 0.15 mmol) was added followed by the addition of trifluoromethanesulfonic anhydride (17 mg, 0.06 mmol). The reaction mixture was stirred for 2 h before warming up to 0° C. Brine (15 mL) was added and the product was extracted with CH$_2$Cl$_2$ (50 mL). The organic layer was dried over Na$_2$SO$_4$ and concentrated to dryness. The crude product was purified via PTLC (33% EtOAc/hexanes) to give 18 mg (50%) of compound F.

Step 6: Compound F (15 mg, 0.026 mmol) was dissolved in CH$_2$Cl$_2$ (1 mL) and cooled to 0° C. MCPBA (29 m g, ca 0.1 mmol) was added. The ice bath was removed and the reaction mixture was stirred at rt overnight. Aqueous NaHCO$_3$ (200 mL) and CH$_2$Cl$_2$ were added and the layers were separated. The organic layer was washed with aq NaHSO$_3$, NaHCO$_3$, H$_2$O, and brine then dried with Na$_2$SO$_4$. The crude product was purified via PTLC (33% EtOAc/hexanes) to give 15 mg (95%) of compound G.

Using the appropriate starting materials in the procedures described above or modifications of those procedures well known to those skilled in the art, the compounds shown in the following tables were prepared. The compound numbers in the TABLE OF COMPOUNDS below correspond to the compound numbers in Table 1.

Compounds Nos. 1-23 were prepared according to the procedures discussed above.

TABLE OF COMPOUNDS

| Compound Number | Structure |
|---|---|
| 1 | |
| 2 | 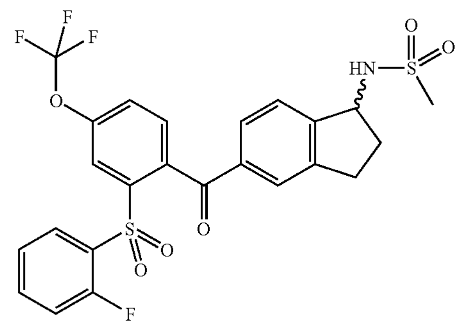 |
| 3 | 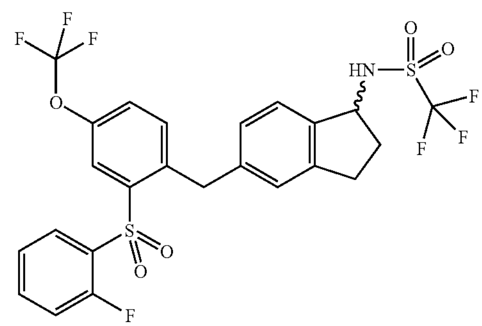 |
| 4 | 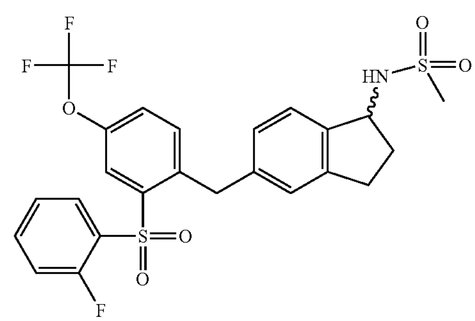 |
| 5 | 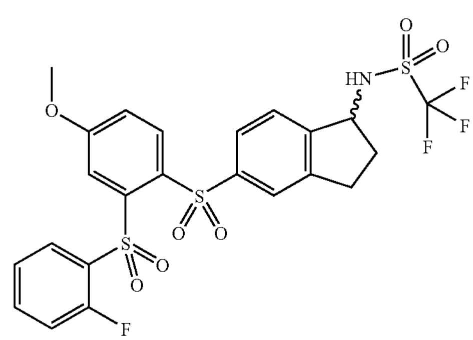 |

TABLE OF COMPOUNDS
| Compound Number | Structure |
|---|---|
| 6 | 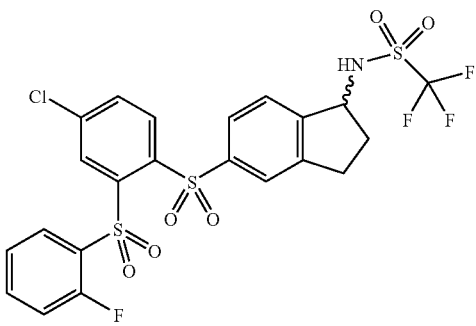 |
| 7 | 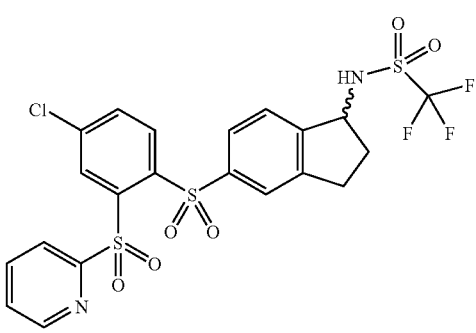 |
| 8 | 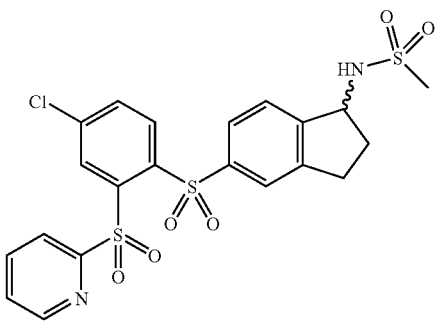 |
| 9 | 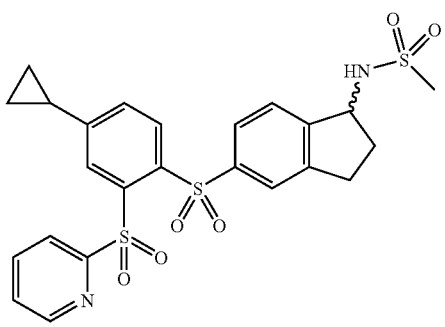 |
| 10 | 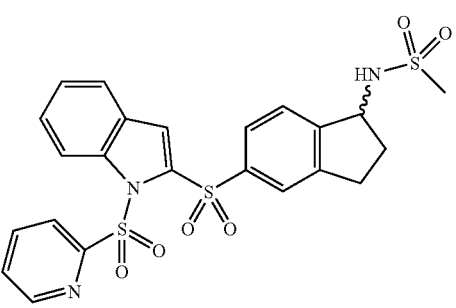 |
| 11 | 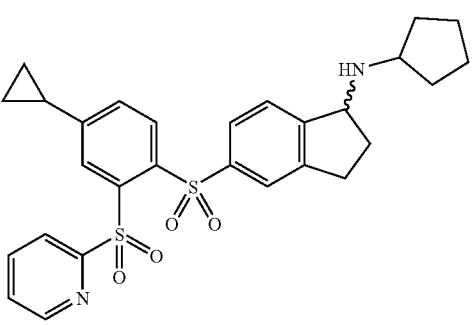 |
| 12 | 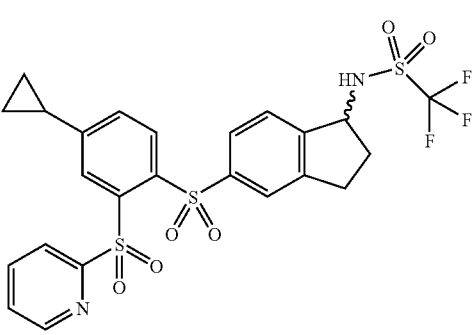 |
| 13 | 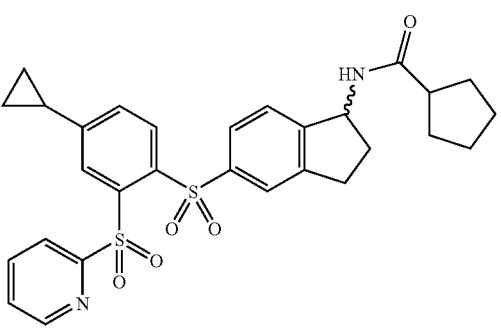 |

TABLE OF COMPOUNDS
Compound Number | Structure
14 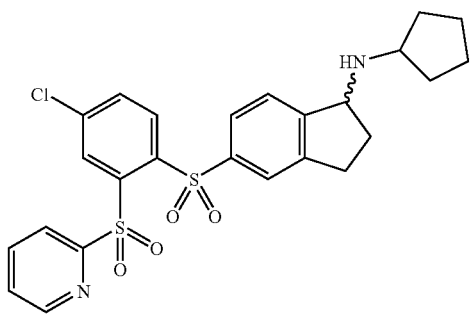
15 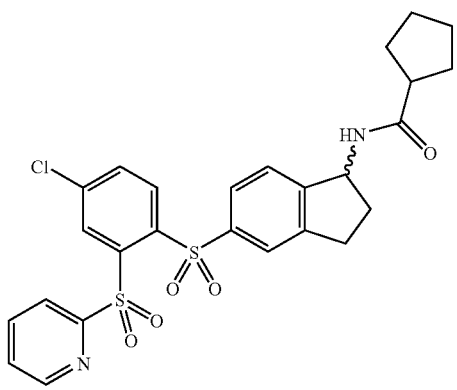
16 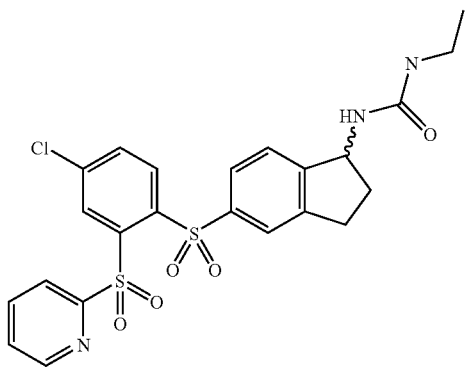
17 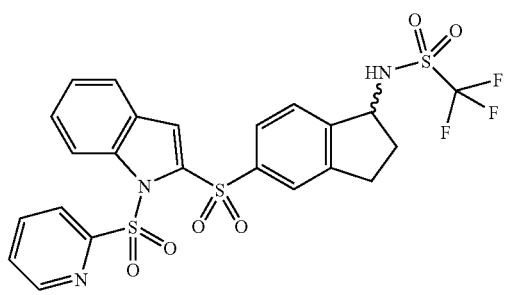
TABLE OF COMPOUNDS
Compound Number | Structure
18 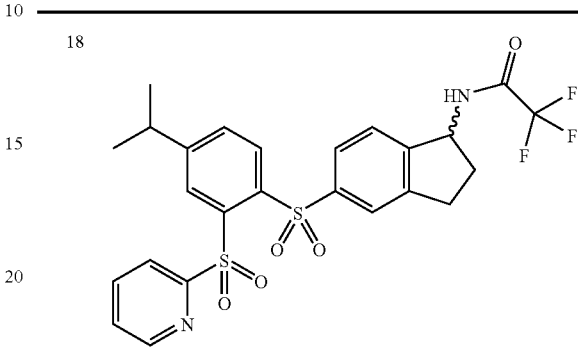
19 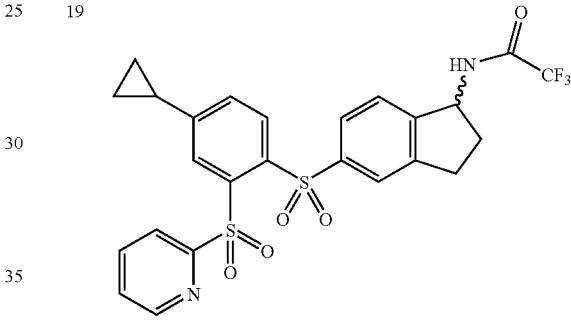
20 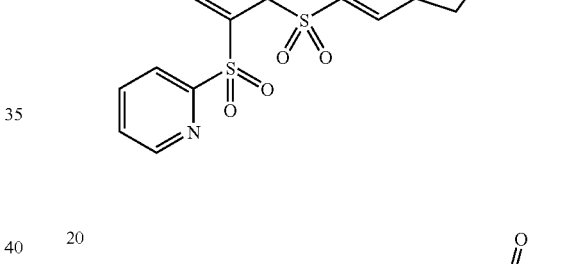
21 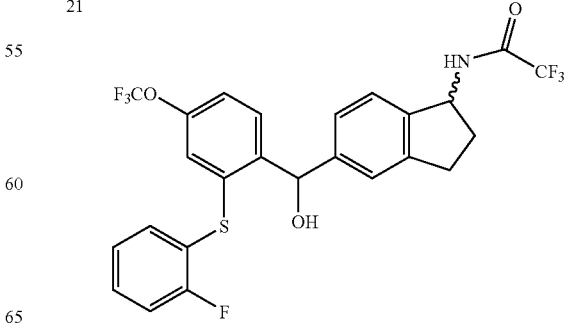

-continued

TABLE OF COMPOUNDS

Compound Number | Structure

22 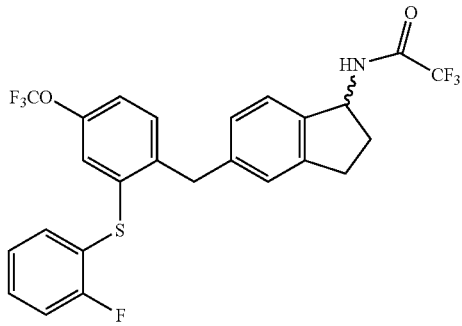

23 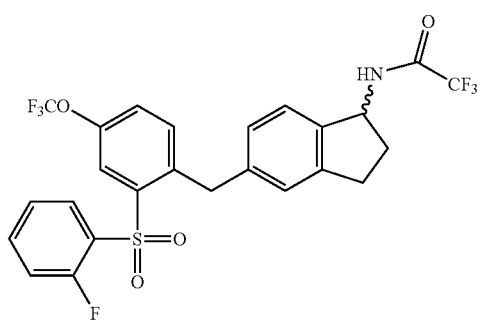

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

We claim:

1. A compound represented by the structural Formula (I):

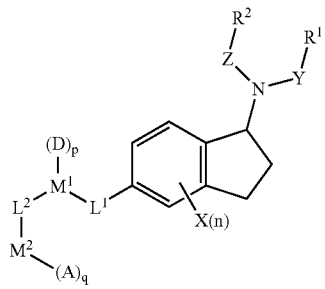

or a pharmaceutically acceptable salt or solvate thereof, wherein:

$R^1$ is selected from the group consisting of hydrogen, substituted or unsubstituted alkyl, —$CF_3$, substituted or unsubstituted alkoxy, —$N(R^3)_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with $(X)_t$ substituent(s);

$R^2$ is selected from the group consisting of hydrogen, substituted or unsubstituted alkyl, —$CF_3$, substituted or unsubstituted alkoxy, —$N(R^3)_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with $(X)_t$ substituent(s); or each $R^3$, which can be the same or different, is independently selected from the group consisting of hydrogen, substituted or unsubstituted alkyl, substituted or unsubstituted cycloalkyl, substituted or unsubstituted heterocycloalkyl, substituted or unsubstituted aryl, substituted or unsubstituted arylalkyl, substituted or unsubstituted heteroaryl, and substituted or unsubstituted heteroarylalkyl, wherein the term "substituted" means being substituted with $(X)_t$ substituent(s);

each X, when present, is independently selected from the group consisting of alkyl, alkenyl, alkynyl, cycloalkyl, heterocycloalkyl, aryl, heteroaryl, aminoalkyl-, —$NR^4R^5$, halo, —$CF_3$, —$OCF_2H$, —$OCF_3$, —$OR^6$, —$C(O)R^6$, —$C(O)OR^6$, —$NR^6C(O)R^7$, —$NR^6C(O)OR^7$, —$C(O)NR^4R^5$, —$NO_2$, —CN, —$S(O)_2R^6$, —$S(O)_2NR^4R^5$ and —$NR^4S(O)_2R^5$;

$R^4$ and $R^5$, which can be the same or different, are each independently selected from the group consisting of H or alkyl, or $R^4$ and $R^5$, taken together with N to which they are each attached, form a 4- to 8- membered heterocycloalkyl moiety optionally having an additional heteroatom selected from the group consisting of N, O and S, wherein the additional N heteroatom, when present, or any ring carbon atom of the heterocycloalkyl moiety can be substituted with H or alkyl;

$R^6$ and $R^7$, which can be the same or different, are each independently selected from the group consisting of H or alkyl;

$L^1$ is selected from the group consisting of —$C(R^2)_2$—, —OC(O)—, —C(O)—, —C(O)O—, —(CH(OR$^2$))—, —$S(O)_2$—, —S(O)—, —S—, —O—, —$N(R^2)$—, —C(O)NH—, —NHC(O)—, —$CF_2$— and —C(=N—OR$^2$)—;

$L^2$ is selected from the group consisting of a covalent bond, —$C(R^2)_2$—, —C(=N—OR$^2$)—, —$S(O)_2$—, —S(O)—, —S—, —C(O)—, —O—, —$N(R^2)$, —C(O)NH—, —NHC(O)—, —OC(O)—, —C(O)O—,—(CH(OR$^2$))— and —$CF_2$—;

$M^1$ is an aryl, heteroaryl, cycloalkyl or heterocycloalkyl moiety wherein said aryl, heteroaryl, cycloalkyl or heterocycloalkyl moiety is substituted with D when p is ≧1;

$M^2$ is an alkyl, cycloalkyl, heterocycloalkyl, aryl or heteroaryl moiety wherein said alkyl, cycloalkyl, heterocycloalkyl, aryl or heteroaryl moiety is substituted with A when q is ≧1;

m is 1-3;

n is 0-3 wherein when n>1, each X can be the same or different and is independently selected;

p is 0-4;

q is 0-5;

t is 0-6 wherein when t>1, each X can be the same or different and is independently selected;

v is 1-3;

A is an optional substituent on $M^2$, each A being independently selected from the group consisting of —Br, —Cl, —F, —$CF_3$, —OH, —$OCF_2H$, —$OCF_3$, alkoxy, substituted or unsubstituted alkyl, substituted or unsubstituted cycloalkyl, —O-substituted or unsubstituted cycloalkyl, substituted or unsubstituted heterocycloalkyl, substituted or unsubstituted aryl, substituted or unsubstituted heteroaryl, —CN, —NO$_2$, —C(O)OR$^4$, —C(O)NR$^4$R$^5$, —NR$^4$C(O)R$^5$, —NR$^4$R$^5$, and —S(O)$_2$R$^2$, wherein the term "substituted" means being substituted with (X)$_t$ and wherein when q>1, each A can be the same or different;

D is an optional substituent on M$^1$, each D being independently selected from the group consisting of —Br, —Cl, —F, —CF$_3$, —OH, —OCF$_2$H, —OCF$_3$, alkoxy, substituted or unsubstituted alkyl, substituted or unsubstituted cycloalkyl, —O-substituted or unsubstituted cycloalkyl, substituted or unsubstituted heterocycloalkyl, substituted or unsubstituted aryl, substituted or unsubstituted heteroaryl, —CN, —NO$_2$, —C(O)OR$^4$, —C(O)NR$^4$R$^5$, —NR$^4$C(O)R$^5$, —NR$^4$R$^5$, and —S(O)$_2$R$^2$, wherein the term "substituted" means being substituted with (X)$_n$ and wherein when p>1, each D can be the same or different;

Y is selected from the group consisting of a covalent bond, —(CR$^6$R$^7$)$_m$—, —S(O)$_2$—, and —C(O)—; and Z is selected from the group consisting of a covalent bond, —(CR$^6$R$^7$)$_v$—, —S(O)$_{0-2}$—, and —C(O)—, with the following provisos:
when L$^2$ is a covalent bond, M$^2$ is directly linked to M$^1$;
when Y is a covalent bond, R$^1$ is directly linked to the nitrogen atom of —N-Z-R$^2$; and
when Z is a covalent bond, R$^2$ is directly linked to the nitrogen atom of —N—Y—R$^1$.

2. A compound according to claim 1, wherein R$^1$ is selected from the group consisting of hydrogen, substituted or unsubstituted alkyl, —N(R$^3$)$_2$, substituted or unsubstituted cycloalkyl, substituted or unsubstituted aryl, substituted or unsubstituted heteroaryl and substituted or unsubstituted heterocycloalkyl, wherein the term "substituted" means being substituted with (X)$_t$, and t is 0-2.

3. A compound according to claim 2, wherein R$^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with (X)$_t$, and t is 0-2.

4. A compound according to claim 1, wherein R$^2$ is selected from the group consisting of hydrogen, substituted or unsubstituted alkyl, —N(R$^3$)$_2$, substituted or unsubstituted cycloalkyl, substituted or unsubstituted heterocycloalkyl, substituted or unsubstituted aryl, and substituted or unsubstituted heteroaryl, wherein the term "substituted" means being substituted with (X)$_t$, and t is 0-2.

5. A compound according to claim 4, wherein R$^2$ is selected from the group consisting of hydrogen, substituted or unsubstituted alkyl, substituted or unsubstituted cycloalkyl, and substituted or unsubstituted heterocycloalkyl, wherein the term "substituted" means being substituted with (X)$_t$, and t is 0-2.

6. A compound according to claim 1, wherein R$^3$ is selected from the group consisting of hydrogen and substituted or unsubstituted alkyl, wherein the term "substituted" means being substituted with (X)$_t$, and t is 0-2.

7. A compound according to claim 6, wherein R$^3$ is hydrogen.

8. A compound according to claim 1, wherein X is selected from the group consisting of alkyl, halogen, —CF$_3$, —OCF$_3$, OH and alkoxy, wherein each X can be the same or different and is independently selected when there is more than one X present.

9. A compound according to claim 1, wherein L$^1$ is selected from the group consisting of —C(R$^2$)$_2$—, —C(O)—, —S(O)$_2$—, —O—, —NR$^2$—, —C(O)NH—, —NHC(O)—, —CF$_2$— and —C(=N—OR$^2$)—.

10. A compound according to claim 9, wherein L$^1$ is selected from the group consisting of —C(R$^2$)$_2$—, —C(O)—, and —S(O)$_2$—.

11. A compound according to claim 1, wherein L$^2$ is selected from the group consisting of a covalent bond, —C(R$^2$)$_2$—, —C(=N—OR$^2$)—, S(O)$_2$—, —C(O)—, —O—, —N(R$^2$)—, —C(O)NH— and —NHC(O)—.

12. A compound according to claim 11, wherein L$^2$ is selected from the group consisting of a covalpnt bond, —C(R$^2$)$_2$—, —S(O)$_2$—, and —C(O)—.

13. A compound according to claim 1, wherein M$^1$ is a moiety selected from the group consisting of aryl and heteroaryl, wherein said aryl or heteroaryl can be optionally substituted with D.

14. A compound according to claim 13, wherein M$^1$ is a moiety selected from the group consisting of phenyl, indolyl, benzofuranyl, dihydrobenzofuranyl, furanyl, thienyl, and pyridinyl.

15. A compound according to claim 1, wherein M$^2$ is a moiety selected from the group consisting of aryl and heteroaryl, wherein said aryl or heteroaryl can be optionally substituted with A.

16. A compound according to claim 15, wherein M$^2$ is a moiety selected from the group consisting of phenyl, furanyl, thienyl, quinolinyl, and pyridinyl.

17. A compound according to claim 1, wherein n is 0-2.

18. A compound according to claim 1 wherein p is 0-2.

19. A compound according to claim 1, wherein q is 0-2.

20. A compound according to claim 1, wherein t is 0-2.

21. A compound according to claim 1, wherein A, which can be the same or different when q>1, is independently selected from the group consisting of —NR$^4$R$^5$, —Cl, —F, —CF$_3$, —OCF$_3$, alkoxy, substituted or unsubstituted alkyl, substituted or unsubstituted heteroaryl, and —S(O)$_2$R$^2$, wherein the term "substituted" means being substituted with (X)$_t$, and t is 0-2.

22. A compound according to claim 21, wherein A, which can be the same or different when q>1, is independently selected from the group consisting of NR$^4$R$^5$, —Cl, —F, —CF$_3$, —OCF$_3$, and substituted or unsubstituted alkyl, wherein the term "substituted" means being substituted with (X)$_t$, and t is 0-2.

23. A compound according to claim 1, wherein D, which can be the same or different when p>1, is independently selected from the group consisting of —Br, —Cl, —F, —CF$_3$, —OH, —OCF$_2$H, —OCF$_3$, alkoxy, substituted or unsubstituted alkyl, substituted or unsubstituted cycloalkyl, —O-cycloalkyl, substituted or unsubstituted heteroalkyl, substituted or unsubstituted heteroaryl, and —S(O)$_2$R$^2$, wherein the term "substituted" means being substituted with (X)$_n$, and n is 0-2.

24. A compound according to claim 23, wherein D, which can be the same or different when p>1, is independently selected from the group consisting of —Cl, —F, —CF$_3$, —OCF$_2$H, —OCF$_3$, substituted or unsubstituted alkyl, cycloalkyl, and heteroaryl, wherein the term "substituted" means being substituted with (X)$_n$, and n is 0-2.

25. A compound according to claim 24, wherein Y represents —S(O)$_2$— or —C(O)—.

26. A compound according to claim 25, wherein Z represents a covalent bond or —S(O)$_2$—.

27. A compound according to claim 1, wherein Z is a covalent bond, R$^2$ is H, n is 0, and R$^1$, L$^1$, L$^2$, M$^1$, M$^2$, q, p, A, D and Y are as defined in the following table:

| # | R¹ | q, A | M¹ (with linking points to L¹, L² and D) | M² (with linking points to L² and A) | L¹ | L² | Y | p, D |
|---|---|---|---|---|---|---|---|---|
| 1 | —CF₃ | 1, —F | D-phenyl(L₁,L₂) | phenyl(L₂,A) | —C(O)— | —S(O)₂— | —S(O)₂— | 1, —OCF₃ |
| 2 | —CH₃ | 1, —F | D-phenyl(L₁,L₂) | phenyl(L₂,A) | —C(O)— | —S(O)₂— | —S(O)₂— | 1, —OCF₃ |
| 3 | —CF₃ | 1, —F | D-phenyl(L₁,L₂) | phenyl(L₂,A) | —CH₂— | —S(O)₂— | —S(O)₂— | 1, —OCF₃ |
| 4 | —CF₃ | 1, —F | D-phenyl(L₁,L₂) | phenyl(L₂,A) | —CH₂— | —S(O)₂— | —S(O)₂— | 1, —OCF₃ |
| 5 | —CF₃ | 1, —F | D-phenyl(L₁,L₂) | phenyl(L₂,A) | —S(O)₂— | —S(O)₂— | —S(O)₂— | 1, —OCH₃ |
| 6 | —CF₃ | 1, —F | D-phenyl(L₁,L₂) | phenyl(L₂,A) | —S(O)₂— | —S(O)₂— | —S(O)₂— | 1, —Cl |
| 7 | —CF₃ | 0 | D-phenyl(L₁,L₂) | pyridyl | —S(O)₂— | —S(O)₂— | —S(O)₂— | 1, —Cl |
| 8 | —CH₃ | 0 | D-phenyl(L₁,L₂) | pyridyl | —S(O)₂— | —S(O)₂— | —S(O)₂— | 1, —Cl |
| 9 | —CH₃ | 0 | D-phenyl(L₁,L₂) | pyridyl | —D(O)₂— | —S(O)₂— | —S(O)₂— | 1, cyclopropyl |

-continued
| # | R¹ | q, A | M¹ (with linking points to L¹, L² and D) | M² (with linking) points to L² and A) | L¹ | L² | Y | p, D |
|---|---|---|---|---|---|---|---|---|
| 10 | —CH₃ | 0 | 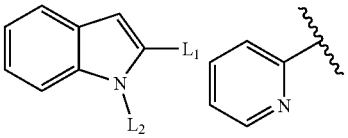 |  | —S(O)₂— | —S(O)₂— | —S(O)₂— | 0 |
| 11 | 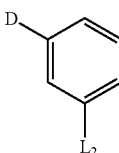 | 0 | 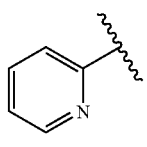 |  | —S(O)₂— | —S(O)₂— | Covalent bond | 1, 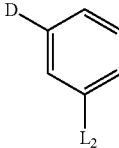 |
| 12 | —CF₃ | 0 | 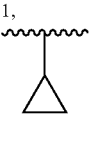 | 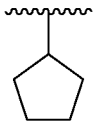 | —S(O)₂— | —S(O)₂— | —S(O)₂— | 1, 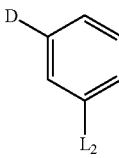 |
| 13 | 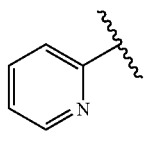 | 0 | 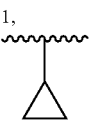 | 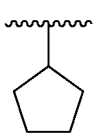 | —S(O)₂— | —S(O)₂— | —C(O)— | 1, 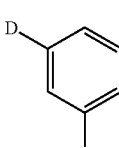 |
| 14 | 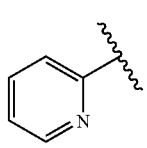 | 0 | 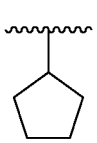 | 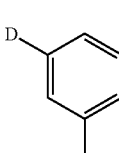 | —S(O)₂— | —S(O)₂— | Covalent bond | 1, Cl |
| 15 | 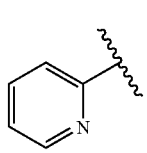 | 0 |  | 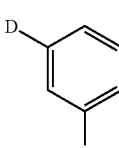 | —S(O)₂— | —S(O)₂— | —C(O)— | 1, Cl |
| 16 | 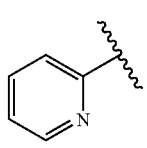 | 0 | 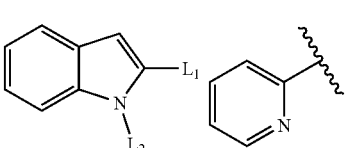 | 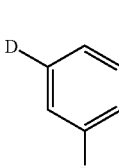 | —S(O)₂— | —S(O)₂— | —C(O)— | 1, Cl |
| 17 | —CF₃ | 0 | 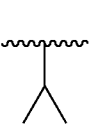 |  | —S(O)₂— | —S(O)₂— | —S(O)₂— | 0 |
| 18 | —CF₃ | 0 |  |  | —S(O)₂— | —S(O)₂— | —C(O)— |  |

-continued

| # | R¹ | q, A | M¹ (with linking points to L¹, L² and D) | M² (with linking) points to L² and A) | L¹ | L² | Y | p, D |
|---|---|---|---|---|---|---|---|---|
| 19 | —CF₃ | 0 | D-phenyl with L₁, L₂ | 2-pyridyl | —S(O)₂— | —S(O)₂— | —C(O)— | 1, cyclopropyl |
| 20 | —CF₃ | 0 | D-phenyl with L₁, L₂ | 2-pyridyl | —S(O)₂— | —S— | —C(O)— | 1, cyclopropyl |
| 21 | —CF₃ | 1, F | D-phenyl with L₁, L₂ | phenyl with L₂, A | —CH(OH)— | —S— | —C(O)— | 1, —OCF₃ |
| 22 | —CF₃ | 1, F | D-phenyl with L₁, L₂ | phenyl with L₂, A | —CH₂— | —S— | —C(O)— | 1, —OCF₃ |
| 23 | —CF₃ | 1, F | D-phenyl with L₁, L₂ | phenyl with L₂, A | —CH₂— | —S(O)₂— | —C(O)— | 1, —OCF₃. |

28. The compound according to claim 1 represented by structural formula IA:

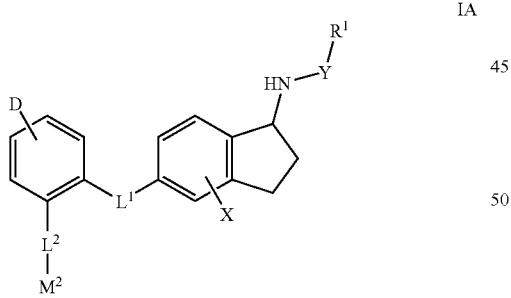

or a pharmaceutically acceptable salt or solvate thereof, wherein:

R¹ is selected from the group consisting of —CF₃, —CH₃, cyclopentyl, and —NC₂H₅;

X is selected from the group consisting of alkyl, halogen, —CF₃, —OH, —OCF₃, and alkoxy;

Y is selected from the group consisting of —S(O)₂—, —C(O)—, and a covalent bond;

L₁ is selected from the group consisting of —S(O)₂—, —CH₂— and —C(O)—;

L₂ is selected from the group consisting of —S(O)₂—, and —CH₂—;

D is selected from the group consisting of —OCF₃, —Cl, cyclopropyl, and isopropyl; and M² is selected from the group consisting of pyridyl and 2-fluorophenyl.

29. The compound according to claim 28, wherein:

R¹ is selected from the group consisting of —CF₃ and —CH₃;

Y is —S(O)₂—;

X is selected from the group consisting of alkyl, halogen, —CF₃, —OH, —OCF₃, and alkoxy;

L₁ is selected from the group consisting of —S(O)₂— and —CH₂—,

L₂ is —S(O)₂—;

D is selected from the group consisting of —OCF₃, —Cl, and cyclopropyl; and

M² is selected from the group consisting of pyridyl and 2-fluorophenyl.

30. The compound according to claim 29, wherein,

R¹ is —CF₃;

X is selected from the group consisting of alkyl, halogen, —CF₃, —OH, —OCF₃, and alkoxy;

Y is —S(O)₂—;

L₁ is —S(O)₂—;

L₂ is —S(O)₂—;

D is selected from the group consisting of —OCF₃, —Cl, and cyclopropyl; and

M² is selected from the group consisting of pyridyl and 2-fluorophenyl.

31. The compound according to claim 1 represented by structural formula IB:

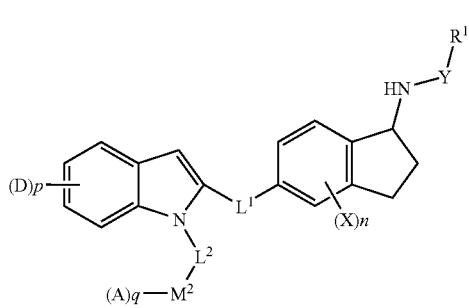

or a pharmaceutically acceptable salt or solvate thereof, wherein:
- $R^1$ is selected from the group consisting of hydrogen, substituted or unsubstituted alkyl, —N($R^3$)$_2$, substituted or unsubstituted cycloalkyl, substituted or unsubstituted aryl, substituted or unsubstituted heteroaryl and substituted or unsubstituted heterocycloalkyl, wherein the term "substituted" means being substituted with (X)$_t$, and t is 0-2;
- $R^3$ is selected from the group consisting of hydrogen and substituted or unsubstituted alkyl, wherein the term "substituted" means being substituted with (X)$_t$, and t is 0-2;
- X is selected from the group consisting of alkyl, halogen, —CF$_3$, —OH, —OCF$_3$, and alkoxy, wherein each X can be the same or different and is independently selected when there are more than one X present;
- Y represents —S(O)$_2$— or —C(O)—;
- $L^1$ is selected from the group consisting of —C($R^2$)$_2$—, —C(O)—, —S(O)$_2$—, —O—, —N($R^2$)—, —C(O)NH—, —NHC(O)—, —CF$_2$— and —C(=N—O$R^2$)—;
- $L^2$ is selected from the group consisting of a covalent bond, —C($R^2$)$_2$—, —C(=N—O$R^2$)—, —S(O)$_2$—, —C(O)—, —O—, —N($R^2$)—, —C(O)NH— and —NHC(O)—;
- $M^2$ is an aryl or heteroaryl moiety wherein said aryl or heteroaryl moiety can be optionally substituted with A;
- n is 0-2;
- p is 0-2; and
- q is 0-2.

32. The compound according to claim 31, or a pharmaceutically acceptable salt or solvate thereof, wherein:
- $R^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with (X)$_t$, and t is 0-2;
- $R^3$ is hydrogen;
- $L^1$ is selected from the group consisting of —C($R^2$)$_2$—, —C(O)—, and —S(O)$_2$—;
- $L^2$ is selected from the group consisting of a covalent bond, —C($R^2$)$_2$—, —S(O)$_2$—, and —C(O)—;
- X is selected from the group consisting of halogen, —CF$_3$, —OH, and —OCF$_3$, wherein each X can be the same or different and is independently selected when there are more than one X present;
- Y represents —S(O)$_2$— or —C(O)—;
- $M^2$, which can be optionally substituted with A, is a moiety selected from the group consisting of phenyl, furanyl, thienyl, quinolinyl and pyridinyl;
- n is 0-2;
- p is 0-2; and
- q is 0-2.

33. The compound according to claim 32, wherein,
- $R^1$ is —CF$_3$;
- X is selected from the group consisting of halo, —CF$_3$, —OH, and —OCF$_3$, wherein each X can be the same or different and is independently selected when there is more than one X present;
- Y is —S(O$_2$)—;
- $L_1$ is —S(O)$_2$—;
- $L_2$ is —S(O)$_2$—; and
- $M^2$ is selected from the group consisting of pyridyl and 2-fluorophenyl.

34. The compound according to claim 1 represented by structural formula IC:

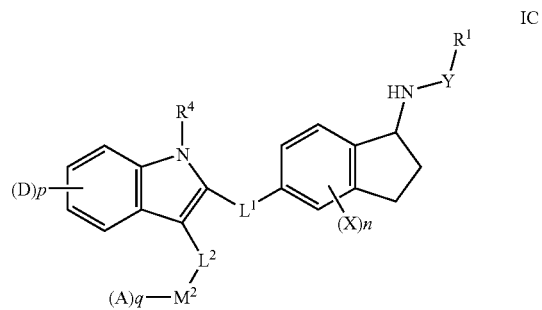

or a pharmaceutically acceptable salt or solvate thereof, wherein:
- $R^1$ is selected from the group consisting of hydrogen, substituted or unsubstituted alkyl, —N($R^3$)$_2$, substituted or unsubstituted cycloalkyl, substituted or unsubstituted aryl, substituted or unsubstituted heteroaryl and substituted or unsubstituted heterocycloalkyl, wherein the term "substituted" means being substituted with (X)$_t$, and t is 0-2;
- $R^3$ is selected from the group consisting of hydrogen and substituted or unsubstituted alkyl, wherein the term "substituted" means being substituted with (X)$_t$, and t is 0-2;
- $R^4$ is hydrogen or alkyl;
- X is selected from the group consisting of alkyl, halogen, —CF$_3$, —OH, —OCF$_3$, and alkoxy, wherein each X can be the same or different and is independently selected when there are more than one X present;
- Y represents —S(O)$_2$— or —C(O)—;
- $L^1$ is selected from the group consisting of —C($R^2$)$_2$—, —C(O)—, —S(O)$_2$—, —O—, —N$R^2$—, —C(O)NH—, —NHC(O)—, —CF$_2$— and —C(=N—O$R^2$)—;
- $L^2$ is selected from the group consisting of a covalent bond, —C($R^2$)$_2$—, —C(=N—O$R^2$)—, —S(O)$_2$—, —C(O)—, —O—, —N($R^2$)—, —C(O)NH— and —NHC(O)—;
- $M^2$ is an aryl or heteroaryl moiety wherein said aryl or heteroaryl moiety can be optionally substituted with A;
- n is 0-2;
- p is 0-2; and
- q is 0-2.

35. The compound according to claim 34, or a pharmaceutically acceptable salt or solvate thereof, wherein:
- $R^1$ is selected from the group consisting of hydrogen, substituted or unsubstituted alkyl, substituted or unsubstituted cycloalkyl, and substituted or unsubstituted heterocycloalkyl, wherein the term "substituted" means being substituted with (X)$_t$, and t is 0-2;

R³ is hydrogen;

R⁴ is hydrogen or alkyl;

L¹ is selected from the group consisting of —C(R²)₂—, —C(O)—, and —S(O)₂—;

L² is selected from the group consisting of a covalent bond, —C(R²)₂—, —S(O)₂—, and —C(O)—;

X is selected from the group consisting of halogen, —CF₃, —OH, and —OCF₃, wherein each X can be the same or different and is independently selected when there are more than one X present;

Y represents —S(O)₂— or —C(O)—;

M², which can be optionally substituted with A, is a moiety selected from the group consisting of phenyl, furanyl, thienyl, quinolinyl and pyridinyl;

n is 0-2;

p is 0-2; and q is 0-2.

36. The compound according to claim 35 wherein,

R¹ is —CF₃;

X is selected from the group consisting of halo, —CF₃, —OH, and —OCF₃, wherein each X can be the same or different and is independently selected when there is more than one X present;

Y is —S(O)₂—;

L₁ is —S(O)₂—;

L₂ is —S(O)₂—; and

M² is selected from the group consisting of pyridyl and 2-fluorophenyl.

37. The compound according to claim 1, wherein said compound is selected from the group consisting of:

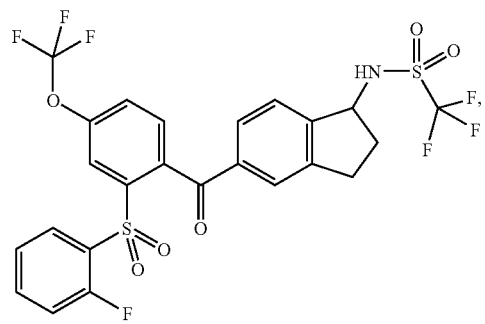

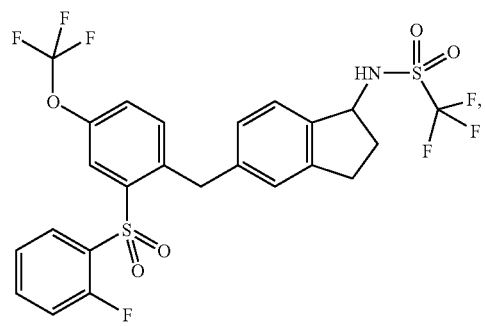

-continued

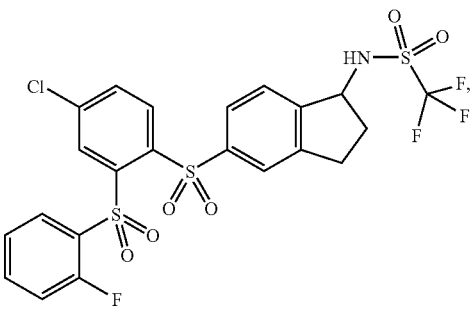

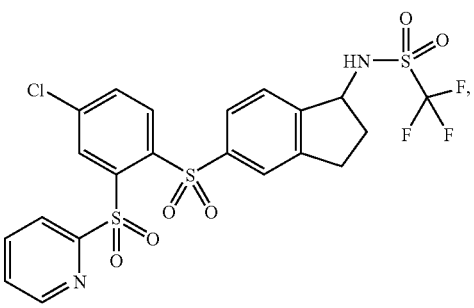

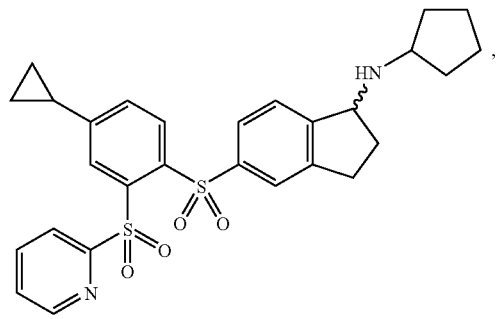

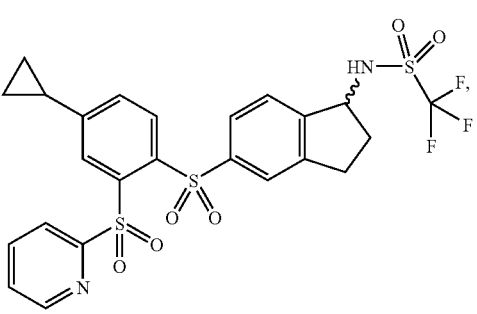

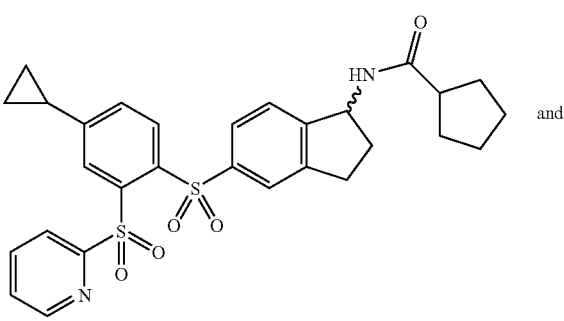

and

-continued

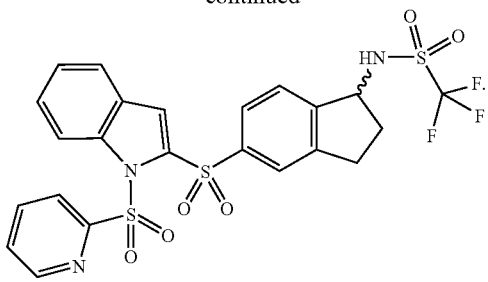

38. A pharmaceutical composition comprising one or more compounds according to claim 1.

39. The pharmaceutical composition according to claim 38, further comprising one or more pharmaceutically acceptable carriers.

40. A method of preparing the pharmaceutical composition of claim 38, said method comprising contacting one or more compounds of formula I with one or more pharmaceutically acceptable carriers.

41. A method of treating inflammatory diseases or immunomodulatory diseases comprising administering to a patient in need of such treatment one or more compounds according to claim 1.

42. The method of treating inflammatory diseases or immunomodulatory diseases according to claim 41, wherein the amount of compound I that is administered is a therapeutically effective amount.

43. The method of treating inflammatory diseases or immunomodulatory diseases according to claim 41, wherein said inflammatory diseases or immunomodulatory diseases are one or more diseases selected from the group consisting of rheumatoid arthritis, systemic lupus erythematosus, multiple sclerosis, hepatitis, psoriasis, atopic dermatitis, vasculitis, neuropathic pain, Crohn's disease, inflammatory bowel disease, asthma, chronic obstructive pulmonary disease (COPD) and bronchitis.

44. A method of treating inflammatory diseases or immunomodulatory diseases comprising co-administering or combining the compound of claim 1 with one or more second agents which can be the same or different from each other, and are independently selected from the group consisting of DMARDS, NSAIDS, COX-2 inhibitors, COX-1 inhibitors, immunosuppressives, BRMs; and other anti-inflammatory agents.

45. The method of treating, inflammatory diseases or immunomodulatory diseases according to claim 44, wherein said DMARDS can be the same or different and are independently selected from the group consisting of methotrexate, azathioptrine leflunomide, pencillinamine, gold salts, mycophenolate mofetil, and cyclophosphamide.

46. The method of treating inflammatory diseases or immunomodulatory diseases according to claim 44, wherein said NSAIDS can be the same or different and are independently selected from the group consisting of piroxicam, naproxen, indomethacin and ibuprofen.

47. The method of inflammatory diseases or immunomodulatory diseases according to claim 44, wherein said COX-1 inhibitor is Piroxicam.

48. The method of treating inflammatory diseases or immunomodulatory diseases according to claim 44, wherein said COX-2 selective inhibitor is refecoxib or celecoxib.

49. The method of treating inflammatory diseases or immunomodulatory diseases according to claim 44, wherein said immunosuppressives can be the same or different and are independently selected from the group consisting of steroids, cyclosporine, Tacrolimus and rapamycin.

50. The method of treating inflammatory diseases or immunomodulatory diseases according to claim 44, wherein said BRMs can be the same or different and are independently selected from the group consisting of etanercept, infliximab, IL-1 antagonists, anti-CD40, anti-CD28, IL-10, and anti-adhesion molecules.

51. The method of treating inflammatory diseases or immunomodulatory diseases according to claim 44, wherein said anti-inflammatory agents can be the same or different and are independently selected from the group consisting of p38 kinase inhibitors, PDE4 inhibitors, TACE inhibitors, chemokine receptor antagonists, and Thalidomide.

52. A method of inflammatory diseases or immunomodulatory diseases comprising co-administering or combining the compound of claim 1 with a second agent selected from the group consisting of Anaprox, Arava, Arthrotec, Azulfidine, Aspirin, Cataflam, Celestone Soluspan, Clinoril, Cortone Acetate, Cuprimine, Daypro, Decadron, Depen, Depo-Medrol, Disalcid, Dolobid, Naprosyn, Gengraf, Hydrocortone, Imuran, Indocin, Lodine, Motrin, Myochrysine, Nalfon, Naprelan, Neoral, Orudis, Oruvail, Pediapred, Plaquenil, Prelone, Relafen, Solu-Medrol, Tolectin, Trilisate and Volataren.

53. The method of treating inflammatory diseases or immunomodulatory diseases according to claim 44, wherein said administration is oral or subcutaneous.

* * * * *

UNITED STATES PATENT AND TRADEMARK OFFICE
CERTIFICATE OF CORRECTION

PATENT NO. : 7,253,189 B2
APPLICATION NO. : 10/721015
DATED : August 7, 2007
INVENTOR(S) : Ling Tong et al.

It is certified that error appears in the above-identified patent and that said Letters Patent is hereby corrected as shown below:

In Claim 12, Col. 64, line 9, change "covalpnt" to -- covalent --.

In Claim 27, Col. 65, last line, change "-D(O)$_2$-" to -- -S(O)$_2$- --.

Signed and Sealed this

Twenty-seventh Day of May, 2008

JON W. DUDAS
*Director of the United States Patent and Trademark Office*